United States Patent
Nilsson et al.

(10) Patent No.: US 9,974,776 B2
(45) Date of Patent: May 22, 2018

(54) ESTROGEN RECEPTOR BETA AGONISTS FOR USE IN TREATING MESOTHELIOMA

(71) Applicant: Karo Pharma AB, Stockholm (SE)

(72) Inventors: Stefan Nilsson, Stockholm (SE); Laura Moro, Novara (IT); Giulia Pinton, Novara (IT); Arcangela Gabriella Manente, Novara (IT)

(*) Notice: Subject to any disclaimer, the term of this patent is extended or adjusted under 35 U.S.C. 154(b) by 0 days. days.

(21) Appl. No.: 15/101,132

(22) PCT Filed: Dec. 4, 2014

(86) PCT No.: PCT/EP2014/076634
§ 371 (c)(1),
(2) Date: Jun. 2, 2016

(87) PCT Pub. No.: WO2015/082643
PCT Pub. Date: Jun. 11, 2015

(65) Prior Publication Data
US 2016/0303087 A1    Oct. 20, 2016

(30) Foreign Application Priority Data

Dec. 5, 2013 (GB) .................................. 1321531.4
Oct. 2, 2014 (GB) .................................. 1417465.0

(51) Int. Cl.
| | |
|---|---|
| A61K 31/42 | (2006.01) |
| A61K 31/40 | (2006.01) |
| A61K 31/28 | (2006.01) |
| A61K 31/422 | (2006.01) |
| C07D 405/12 | (2006.01) |
| A61K 31/4045 | (2006.01) |
| A61K 31/519 | (2006.01) |
| A61K 33/24 | (2006.01) |

(52) U.S. Cl.
CPC ........ *A61K 31/422* (2013.01); *A61K 31/4045* (2013.01); *A61K 31/519* (2013.01); *A61K 33/24* (2013.01); *C07D 405/12* (2013.01)

(58) Field of Classification Search
CPC ....... A61K 31/42; A61K 31/28; C07D 405/12
USPC ........................................ 514/378, 414, 492
See application file for complete search history.

(56) References Cited

FOREIGN PATENT DOCUMENTS

| EP | 2143432 A1 | 1/2010 |
|---|---|---|
| WO | 0241835 A2 | 5/2002 |
| WO | 02072561 A1 | 9/2002 |
| WO | 03044006 A1 | 5/2003 |
| WO | 2004094401 A1 | 11/2004 |
| WO | 2006019831 A1 | 2/2006 |
| WO | 2006044176 A1 | 4/2006 |
| WO | 2006062876 A2 | 6/2006 |
| WO | 2006088716 A1 | 8/2006 |
| WO | 2007062876 A1 | 6/2007 |
| WO | 2008033894 A2 | 3/2008 |
| WO | 2008043567 A1 | 4/2008 |
| WO | 2009012954 A1 | 1/2009 |
| WO | 2009055734 A1 | 4/2009 |
| WO | 2009121910 A1 | 10/2009 |
| WO | 2009124968 A1 | 10/2009 |
| WO | 2009127686 A1 | 10/2009 |
| WO | 2010031852 A1 | 3/2010 |
| WO | 2011042473 A2 | 4/2011 |
| WO | 2011042474 A1 | 4/2011 |
| WO | 2011042475 A1 | 4/2011 |
| WO | 2011042477 A1 | 4/2011 |
| WO | 2013017619 A1 | 2/2013 |
| WO | 2013033392 A1 | 3/2013 |

OTHER PUBLICATIONS

International Search Report and Written Opinion of the International Searching Authority for International Application No. PCT/EP2014/076634; International Filing Date: Dec. 4, 2014; Date of Mailing: Mar. 31, 2015; 13 pages.
Jagadeeswaran et al.; "Functional Analysis of c-Met/Hepatocyte Growth Factor Pathway in Malignant Pleural Mesothelioma"; Cancer Res., vol. 66, No. 1; Jan. 1, 2006; pp. 352-361.
Kitazono-Saitoh et al.; "Interaction and Cross-Resistance of Cisplatin and Pemetrexed in Malignant Pleural Mesothlioma Cell Lines"; Oncology Reports, vol. 28; 2012; pp. 33-40.
Manente et al., "Estrogen Receptor β Activation Impairs Mitochondrial Oxidative Metabolism and Affects Malignant Mesothelioma Cell Growth in vitro and in vivo" Oncogenesis, vol. 2, e72; doi:10.1038/oncsis.2013.32, published online Sep. 23, 2013, pp. 1-10.
Pinton et al.; "Agonist activation of estrogen receptor beta (ERβ) sensitizes malignant pleural mesothelioma cells to cisplatin cytotoxicity"; Molecular Cancer, vol. 13:227; Oct. 2, 2014; pp. 1-14.
Pinton et al.; "Perifosine as a Potential Novel Anti-Cancer Agent Inhibits EGFR/MET-AKT Axis in Malignant Pleural Mesothelioma"; PLOS ONE, vol. 7, No. 5: e36856. doi:10.1371/journal.pone.0036856; published May 10, 2012; pp. 1-7.
Pinton et al.; "Therapies currently in Phase II trials for malignant pleural mesothelioma"; Expert Opinion on Investigational Drugs, vol. 22, No. 10; Oct. 2013; pp. 1-10.
Santoro et al.; "Pemetrexed Plus Cisplatin or Premetrexed Plus Carboplatin for Chemonaive Patients with Malignant Pleural Mesothelioma: Results of the International Expanded Access Progam"; J. Thorac. Oncol., vol. 3. No. 7; Jul. 2008; p. 756-763.

(Continued)

*Primary Examiner* — Raymond Henley, III

(57) ABSTRACT

The invention provides a treatment of mesothelioma, especially malignant pleural mesothelioma, using an estrogen receptor β subtype (ERβ) agonist, wherein the treatment comprises administering the ERβ agonist to the patient, and then after a time, t, of up to 24 hours; administering a platinum-containing anti-cancer drug to the patient. The invention also provides an ERβ agonist and a platinum-containing anti-cancer drug for use in the treatment of mesothelioma in a patient, wherein the treatment comprises administering the ERβ agonist to the patient, and then after a time, t, of up to 24 hours, administering the platinum-containing anti-cancer drug to the patient; and a kit comprising a platinum-containing anti-cancer drug and an ERβ agonist.

18 Claims, 12 Drawing Sheets

(56) References Cited

OTHER PUBLICATIONS

Altomare et al., "Human and Mouse Mesotheliomas Exhibit Elevated AKT/PKB Activity, Which can be Targeted Pharmacologically to Inhibit Tumor Cell Growth" Oncogene, 24, (2005), pp. 6080-6089.

Arafa et al., "Tangeretin Sensitizes Cisplatin-Resistant Human Ovarian Cancer Cells through Downregulation of Phosphoinositide 3-Kinase/Akt Signaling Pathway" Cancer Research, 69, (2009), pp. 8910-8917.

Bossard et al., "Potential Role of Estrogen Receptor Beta as a Tumor Suppressor of Epithelial Ovarian Cancer" ERβ Controls Ovarian Carcinogenesis, vol. 7, Issue 9, Sep. 2012, 10 Pages.

Cedres et al., "Exploratory Analysis of Activation of PTEN-PI3K Pathway and Downstream Proteins in Malignant Pleural Mesothelioma (MPM)" Lung Cancer, 77, (2012), pp. 192-198.

Ceresoli et al.; "Phase II Study of Pemetrexed Plus Carboplatin in Malignant Pleural Mesothelioma"; J. Clin. Oncol., vol. 24, No. 9; Mar. 20, 2006; pp. 1443-1448.

Hahne et al., "Downregulation of AKT Reverses Platinum Resistance of Human Overian Cancers in vitro" Oncology Reports, 28, (2012), pp. 2023-2028.

Halon et al., "Loss of Estrogen Receptor Beta Expression Correlates with Shorter Overall Survival and Lack of Clinical Response to Chemotherapy in Ovarian Cancer Patients" Anticancer Research, 31, (2011), pp. 711-718.

Hartman et al., "Combined Treatment with Cisplatin and Sirolimus to Enhance Cell Death in Human Mesothelioma" The Journal of Thoracic and Cardiovascular Surgery, vol. 139, No. 5, (2009), pp. 1233-1240.

Hoda et al., "Temsirolimus Inhibits Malignant Pleural Mesothelioma Growth in Vitro and in Vivo" Journal of Thoracic Oncology, vol. 6, No. 5, (2011), pp. 852-863.

Laura Moro; "Agonist activation of estrogen receptor beta (ERb) sensitizes malignant pleural mesothelioma cells to cisplatin cytotoxicity"; Presentation from the 12th International Conference of the International Mesothelioma Interest Group; Oct. 21-24, 2014.

Manente et al.; "Estrogen receptor beta activation impairs mitochondrail oxidative energy metabolism and affects malignant mesothelioma cell proliferation in vitro and in vivo"; Poster from the 11th International Conference of the IMIG; Sep. 12, 2012.

Manente et al.; Abstract Book of the 11th International Conference of the International Mesothelioma Interest Group; p. 86; publication date unknown.

Pinton et al.; "Agonist Activiation of Estrogen Receptor Beta Sensitizes Malignant Pleural Mesothelioma Cells to Cisplatin Cytoxicity"; Molecular Cancer, vol. 13 No. 227; 2014; pp. 1-14.

Pinton et al.; "Targeting estrogen receptor beta for treatment of pleural malignant mesothelioma"; Poster from 11th International Conference of the International Mesothelioma Interest Group; Sep. 12, 2012.

Pinton et al.; Abstract Book of the 11th International Conference of the International Mesothelioma Interest Group; pp. 104-105; publication date unknown.

Pinton et al; "Agonist activation of estrogen receptor beta (ERb) sensitizes malignant pleural mesothelioma cells to cisplatin cytotoxicity"; Abstract from the 12th International Conference of the International Mesothelioma Interest Group; uncertain if published.

Wang et al.; "Molecular Imaging Revals a Role for AKT in Resistance to Cisplatin for Ovarian Endometrioid Adenocarcinoma"; Clinical Cancer Research, vol. 19; Jan. 2013; pp. 158-169.

| Day 1 | Treatment | Day 15 | 16 | 17 | 18 | 19 | 20 | 21 | 22 | 23 | 24 | 25 | 26 | 27 | 28 | 29 | 30 | 31 | 32 | 33 | 34 | Day 35 |
|---|---|---|---|---|---|---|---|---|---|---|---|---|---|---|---|---|---|---|---|---|---|---|
| REN cells injected | Compound (I) (10 mg/kg) | x | x | x | x | x | x | x | x | x | x | x | x | x | x | x | x | x | x | x | x | x |
| | cisplatin (5 mg/kg) | | | | x | | | | | | | x | | | | | | | | | | |
| | pemetrexed (150 mg/kg) | | | | | x | x | x | x | x | | x | x | x | x | x | | | | | | |

Figure 5A

| Treatment / Cell cycle phase | Go/G1 | S | G2/M | Dead cells (sub G1) |
|---|---|---|---|---|
| Control | 39 ± 1.9 | 33 ± 2.4 | 25 ± 0.5 | 3 ± 1 |
| 100 μM cisplatin, (24 hrs) | 39 ± 0.9 | 31 ± 2.3 | 22 ± 3.2 | 8 ± 2 |
| 10 nM Compound (I) (2 hrs) + normal medium (24 hrs) | 36 ± 1.9 | 29 ± 0.9 | 27 ± 0.9 | 8 ± 2 |
| 10 nM Compound (I) (2 hrs) + 100 μM cisplatin (24 hrs) | 48 ± 0.8 | 2± 2 | 28 ± 2.9 | 22 ± 1 |

ESTROGEN RECEPTOR BETA AGONISTS FOR USE IN TREATING MESOTHELIOMA

CROSS-REFERENCE TO RELATED APPLICATIONS

This application is a National Stage application of PCT/EP2014/076634, filed Dec. 4, 2014, which claims the benefit of Foreign Application Nos. GB 1417465.0, filed Oct. 2, 2014, and GB 1321531.4, filed Dec. 5, 2013, all of which are incorporated by reference in their entirety herein.

FIELD OF INVENTION

The present invention relates to a treatment of mesothelioma, especially malignant pleural mesothelioma, using an estrogen receptor β subtype agonist (ERβ agonist) and a platinum-containing anti-cancer drug.

BACKGROUND OF THE INVENTION

Mesothelioma is a cancer of mesothelial cells of the lungs and/or abdomen. Malignant pleural mesothelioma (MPM) is the most common form of mesothelioma and it is associated with exposure to asbestos. Currently rates of MPM are rising and estimates indicate that the incidence of MPM will peak within the next 10-15 years in the western world, while in Japan the peak is predicted not to occur until 40 years from now (Robinson B M., Ann Cardiothorac Surg 2012; 1(4): 491-6; Prazakova S, Thomas P S, Sandrini A, Yates D H., Clin Respir J 2013; 8(1):1-10). Although the use of asbestos has been banned in many countries around the world, production of, and exposure to, asbestos is still present with locally high incidences of mesothelioma (Stayner L, Welch L S, Lemen R., Annu Rev Public Health 2013; 34:205-16). Carbon nanotubes have also become of potential concern for causing mesothelioma, as they have been reported to display 'asbestos-like' pathogenicity with mesothelioma induction potential (Donaldson K, Poland C A, Murphy F A, Macfarlane M, Chernova T, Schinwald A., Adv Drug Deliv Rev 2013; 65(15):2078-86; Dumortier H., Adv Drug Deliv Rev. 2013; 65(15):2120-26).

MPM is an extremely difficult disease to treat, with a median overall survival time ranging from 9 to 17 months, regardless of disease stage (Campbell N P, Kindler H L., Semin Respir Crit Care Med 2011; 32:102-10; Mossman B T, et al, Am J Pathol 2013; 182(4):1065-77). The combination of cisplatin and pemetrexed has been established as the current standard of care (SOC). However, only 40% of treated patients show response to this therapy, with an overall median survival of 12.1 months (Vogelzang N J, et al., J Clin Oncol 2003; 21:2636-44). Various chemotherapy agents have been used, either as monotherapy or as part of polytherapy, as a second line of treatment for MPM, but none has been successfully validated.

In Pinton, G., et al, Abstract Book of the 11th International Conference of the International Mesothelioma Interest Group, September 2012, pages 104-105, an ERβ agonist, KB9520, is described as inhibiting propagation of the human ERβ positive REN mesothelioma cell line in culture by blockage of the cell cycle at G1. In the poster to which that abstract relates, Pinton et al, presented evidence that an ERβ agonist potentiated the anti-proliferative effect of cisplatin and pemetrexed on human mesothelioma REN cells in vitro, and in vivo in mice.

There remains a need for improved or alternative treatments for clinical management of mesothelioma.

SUMMARY OF THE INVENTION

This invention provides an ERβ agonist for use in the treatment of mesothelioma in a patient, wherein the treatment comprises:
 a) administering the ERβ agonist to the patient, and then after a time, t, of up to 24 hours,
 b) administering a platinum-containing anti-cancer drug to the patient.

The present inventors have surprisingly found that an ERβ agonist is particularly effective in combination with a platinum-containing anti-cancer drug for the treatment of malignant mesotheliomas when the ERβ agonist is administered at a time, t, of up to 24 hours before the administration of the platinum-containing anti-cancer drug. This surprising synergistic effect is only present when the ERβ agonist is administered first: the effect is not present when the platinum-containing anti-cancer drug is administered before the ERβ agonist.

The present invention also provides a method for the treatment of mesothelioma in a patient, which comprises:
 a) administering an ERβ agonist to the patient, and then after a time, t, of up to 24 hours,
 b) administering a platinum-containing anti-cancer drug to the patient.

The present invention further provides an ERβ agonist for the manufacture of a medicament for the treatment of mesothelioma in a patient, wherein the treatment comprises:
 a) administering the ERβ agonist to the patient, and then after a time, t, of up to 24 hours,
 b) administering a platinum-containing anti-cancer drug to the patient.

The present invention further provides an ERβ agonist and a platinum-containing anti-cancer drug for use in the treatment of mesothelioma in a patient, wherein the treatment comprises:
 a) administering the ERβ agonist to the patient, and then after a time, t, of up to 24 hours,
 b) administering the platinum-containing anti-cancer drug to the patient.

The present invention further provides a kit comprising a platinum-containing anti-cancer drug and an ERβ agonist.

BRIEF DESCRIPTION OF THE DRAWINGS

FIG. 5A shows the cell cycle phase results of REN cells that were treated for 24 hours with cisplatin (100 μM) or pre-treated 2 hours with Compound (I) (10 nM) followed by wash-off and continued growth in normal medium±cisplatin (100 μM), for an additional 24 hours.

DETAILED DESCRIPTION OF INVENTION

Figure 1A:
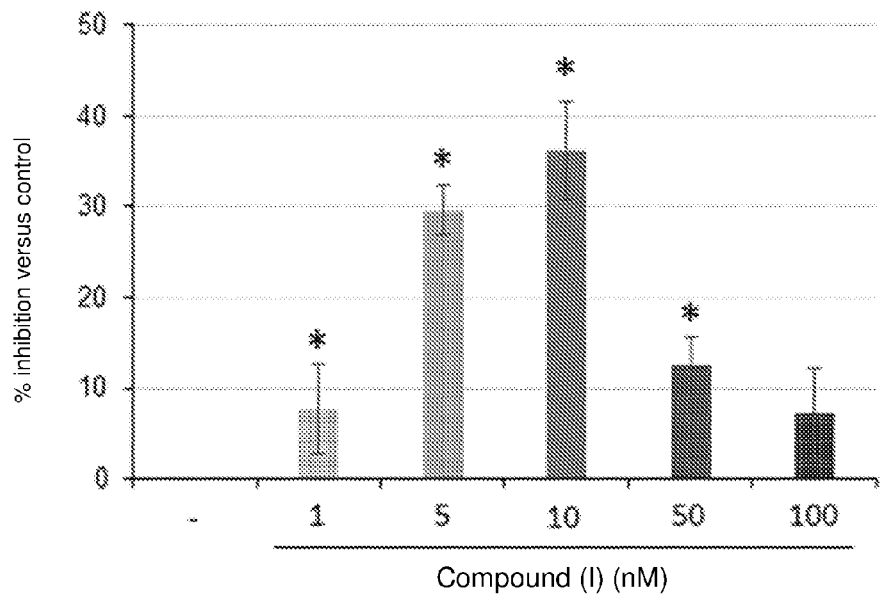
FIG. 1A shows the percentage of growth inhibition of malignant pleural mesothelioma derived REN cells after 24 hours treatment with different doses of Compound (I) (range 1-100 nM) versus untreated cells. Each bar represents mean+/−standard deviation (s.d); *p≤0.05.

The present invention provides an ERβ agonist for use in the treatment of mesothelioma in a patient, wherein the treatment comprises:
  a) administering the ERβ agonist to the patient, and then after a time, t, of up to 24 hours,
  b) administering a platinum-containing anti-cancer drug to the patient.

It has been found by the present inventors that Compound (I), a selective ERβ agonist, has anti-proliferative effects in MPM cell lines in vitro. It has been found that the anti-proliferative effect of Compound (I) is associated with its effect on ERβ and its efficacy was related to the levels of ERβ endogenously expressed. Compound (I) has no anti-proliferative effect on the ERβ positive mesothelium derived MET5A cells.

The inventors have now additionally found that Compound (I), a selective ERβ agonist, brings about an enhanced growth inhibitory effect of cisplatin/pemetrexed in REN cells in vitro and vivo in mice.

The present inventors have surprisingly found that the order of administration of the ERβ agonist and the cisplatin (or a cisplatin/pemetrexed combination) is key to the improved effectiveness of the treatment: exposure of REN cells to the ERβ agonist prior to cisplatin resulted in synergistic inhibition of malignant mesothelioma cell proliferation and survival, whereas the reverse order of drug exposure did not provide this enhancement.

Furthermore, MPM cells preconditioned with ERβ agonist were more sensitive to low-dose cisplatin cytotoxicity. When the ERβ agonist is administered before the cisplatin it surprisingly acts as a chemosensitizer, increasing cisplatin cytotoxicity. The invention may thus allow for a milder SOC (cisplatin) regimen in patients without loss of anti-tumor efficacy. As cisplatin is associated with serious toxicity, and because the majority of patients diagnosed with MPM are older than 65 years, their health condition may not allow the standard chemo dosing regimen of cisplatin/pemetrexed. Therefore, the present findings may find particular utility in patients that cannot tolerate the standard cisplatin/pemetrexed dose regimen.

The present inventors have further found that malignant and non-malignant cells have strikingly different responses to cisplatin and the ERβ agonist: the response to Compound (I) was neutral in non-malignant mesothelium derived cells, whereas it inhibited proliferation and tumor growth of MPM cells.

Further, pre-treatment with Compound (I) followed by cisplatin treatment resulted in significantly increased cell sensitivity to cisplatin in MPM cells, whereas in non-malignant mesothelium-derived cells it counteracted cisplatin cytotoxicity. Therefore an ERβ agonist can be used to reduce the toxicity of the platinum-containing anti-cancer drug in the normal cells of a patient, and thereby protect the normal cells from the adverse effects of the platinum-containing anti-cancer drug.

Therefore, an ERβ agonist has utility in reducing the toxicity of a platinum-containing anti-cancer drug in a patient. The current invention thus provides an ERβ agonist for use in the reduction of toxicity of a platinum-containing anti-cancer drug in non-cancerous cells of a patient, wherein the treatment comprises:

a) administering the ERβ agonist to the patient, and then after a time, t, of up to 24 hours,
b) administering a platinum-containing anti-cancer drug to the patient.

The invention also provides a method of reducing the side effects of a platinum-containing anti-cancer drug comprising the step of administering an ERβ agonist shortly before administering the platinum-containing anti-cancer drug. For example, the ERβ agonist is given up to 24 hours before the platinum-containing anti-cancer drug, for example from 1 to 4 hours before, for example 2 hours before.

In summary, the present inventors have surprisingly shown that an ERβ agonist acts as a chemosensitizer and that the order of drug administration in combination with cisplatin is essential for the synergistic efficacy observed in vitro.

Further, they have surprisingly found that Compound (I) had no cytotoxic effect in ERβ expressing non-malignant mesothelial MET5A cells and, moreover, Compound (I) diminishes cisplatin cytotoxicity in these cells. Therefore, there is the possibility to add an ERβ agonist to the present cisplatin treatment for MPM without adding significant additional toxicity.

ERβ Agonists

An "ERβ agonist" is a compound that exhibits a potency in the range of $EC_{50}$ 0.1 to 10,000 nM at the estrogen receptor β-subtype. Preferred ERβ agonist compounds for use in the invention display a potency at the estrogen receptor β-subtype at lower concentrations within that $EC_{50}$ range, for example a potency in the range of $EC_{50}$ 0.1 to 100 nM. Preferred ERβ agonist compounds of the invention are those which are selective for the estrogen receptor β-subtype over the estrogen receptor α-subtype. A selective ERβ agonist is a compound that displays selectivity for the estrogen receptor β-subtype of 20 or greater compared to the estrogen receptor α-subtype, or more preferably of 50 or greater compared to the estrogen receptor α-subtype. In certain preferred embodiments, an ERβ agonist compound for use in the invention is greater than 100 times selective, greater than 200 times selective; greater than 300 times selective; or greater than 500 times selective (as calculated based on $EC_{50}$ potency values) for the estrogen receptor β-subtype over the estrogen receptor α-subtype.

ERβ agonists are known in the art. For example, an ERβ agonist for use in the invention may be a compound described as an ERβ agonist in any one of WO 2002/072561, WO 03/044006, WO 2004/094401, WO 2006/08871, WO 2006/019831, WO 2006/044176, WO 2006/062876, WO 2007/062876, EP 2143432, WO 2008/033894, WO 2008/043567, WO 2009/012191, WO 2009/012954, WO 2009/055734, WO 2009/124968, WO 2009/127686, WO 2010/031852, WO 2011/042473, WO 2011/042474, WO 2011/042475, WO 2011/042477 and WO 2013/017619, the whole contents of which are herein incorporated by reference.

Preferably the ERβ agonist is a compound described as an ERβ agonist in WO 2009/127686 or WO 2006/062876. For example, it may be a compound of formula (III) or a pharmaceutically acceptable ester, amide, carbamate, solvate or salt thereof, including a salt of such an ester, amide or carbamate, and a solvate of such an ester, amide, carbamate or salt,

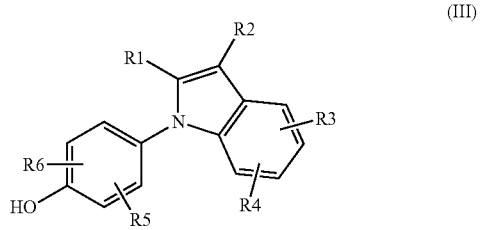

(III)

wherein $R^1$ is selected from the group consisting of halogen, cyano, nitro, $OR^A$, $N(R^B)_2$, —$C(O)C_{1-4}$alkyl, —$SO_2C_{1-4}$alkyl, $C_{1-6}$alkyl, $C_{2-6}$alkenyl, $C_{2-6}$alkynyl, halo$C_{1-6}$alkyl, dihalo$C_{1-6}$alkyl, trihalo$C_{1-6}$alkyl, halo$C_{2-6}$alkenyl, dihalo$C_{2-6}$alkenyl, trihalo$C_{2-6}$alkenyl, cyano$C_{1-6}$alkyl, $C_{1-4}$alkoxy$C_{1-6}$ alkyl, $C_{3-8}$cycloalkyl, $C_{3-8}$cycloalkyl$C_{1-6}$alkyl, phenyl, benzyl, and 5-10 membered heterocyclyl, wherein said phenyl, benzyl or heterocyclyl group can be either unsubstituted or substituted with from 1 to 3 substituents, each substituent being selected from the group consisting of $OR^A$, halogen, cyano, nitro, —$C(O)C_{1-4}$alkyl, $C_{1-6}$alkyl, $C_{2-6}$alkenyl, $C_{2-6}$alkynyl, halo$C_{1-6}$ alkyl, dihalo$C_{1-6}$alkyl and trihalo$C_{1-6}$alkyl;

$R^2$ is selected from the group consisting of halogen, cyano, nitro, $OR^A$, $N(R^B)_2$, $N(OH)_2$, —$C(O)C_{1-4}$alkyl optionally substituted with from 1 to 3 halogens, —$SO_2C_{1-4}$alkyl, —$C(O)NH$—$OH$, —$C(NH_2)$=$N$—$OH$, —$C(CO_2H)$=$N$—$OH$, —$C(NH_2)$=$NH$, —$C(NH\ C_{1-4}alkyl)$=$NH$, —$C(O$—$C_{1-4}alkyl)$=$NH$, —$C(NH_2)$=$N$—$NH_2$, —$NH$—$C(NH_2)$=$NH$, —$NH$—$C(O)NH_2$, —$N$=$C($—$NH$—$CH_2CH_2$—$NH$—), —$S$—$CN$, —$S$—$C(NH_2)$=$NH$, —$S$—$C(NH_2)$=$N$—$OH$, —$CO_2H$, —$CH_2$—$CO_2H$, —$CH(OH)CO_2H$, —$C(O)CO_2H$, $SO_3H$, $CH_2SO_3H$, $C_{1-6}$alkyl, halo$C_{1-6}$alkyl, dihalo$C_{1-6}$alkyl, trihalo$C_{1-6}$alkyl, cyano$C_{1-6}$alkyl, $C_{1-4}$alkoxy$C_{1-6}$ alkyl, $C_{2-6}$alkenyl, $C_{2-6}$alkynyl, $C_{3-8}$cycloalkyl, $C_{3-8}$cycloalkyl$C_{1-6}$ alkyl, phenyl, benzyl and 5-10 membered heterocyclyl wherein said phenyl, benzyl or heterocyclyl group can be either unsubstituted or substituted with from 1 to 3 substituents each substituent being selected from the group consisting of $OR^A$, halogen, cyano, nitro, $C_{1-6}$alkyl, $C_{2-6}$alkenyl, $C_{2-6}$alkynyl, halo$C_{1-6}$alkyl, dihalo$C_{1-6}$alkyl and trihalo$C_{1-6}$alkyl; provided that if one of $R^1$ and $R^2$ represents halogen, the other must represent a group other than halogen;

each of $R^3$, $R^4$, $R^5$ and $R^6$ is independently selected from the group consisting of hydrogen, $OR^A$, halogen, cyano, nitro, $C_{1-6}$alkyl, $C_{2-6}$alkenyl, $C_{2-6}$alkynyl, halo$C_{1-6}$alkyl, dihalo$C_{1-6}$alkyl and trihalo$C_{1-6}$alkyl;

each $R^A$ is independently selected from the group consisting of hydrogen, $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, $C_{6-10}$aryl and $C_{6-10}$aryl$C_{1-6}$alkyl, each optionally substituted by from 1 to 3 halogen atoms; and each $R^B$ is independently selected from the group consisting of hydrogen, $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, $C_{6-10}$aryl and $C_{6-10}$aryl$C_{1-6}$alkyl, each optionally substituted by from 1 to 3 halogen atoms;

with the proviso that the compound of formula (III) is not

4-[3-(4,5-Dihydro-1H-imidazol-2-yl)-2-(3,5-dimethyl-isoxazol-4-yl)-indol-1-yl]-phenol;

1-(4-Hydroxy-phenyl)-2-(4-methyl-imidazol-1-yl)-1H-indole-3-carbonitrile;

1-(4-Hydroxy-phenyl)-2-(1H-pyrazol-3-yl)-1H-indole-3-carbonitrile;

1-(3-Chloro-4-hydroxy-phenyl)-2-(1-methyl-1H-pyrazol-4-yl)-1H-indole-3-carbonitrile;

1-(4-Hydroxy-phenyl)-2-prop-1-ynyl-1H-indole-3-carboxylic acid amide; or 1-(4-Hydroxy-phenyl)-2-thiazol-2-yl-1H-indole-3-carboxylic acid.

Preferably in the compound of formula (III), $R^1$ is selected from the group consisting of $OR^A$, $N(R^B)_2$, $-C(O)C_{1-4}$alkyl, $C_{1-6}$alkyl, $C_{2-6}$alkenyl, $C_{2-6}$alkynyl, halo$C_{1-4}$alkyl, dihalo$C_{1-4}$alkyl, trihalo$C_{1-4}$alkyl, halo$C_{2-4}$alkenyl, dihalo$C_{2-4}$alkenyl, trihalo$C_{2-4}$alkenyl, phenyl, and 5-6 membered heterocyclyl, wherein said phenyl or heterocyclyl group may be either unsubstituted or substituted as above by 1 to 3 substituents selected from the group consisting of $OR^A$, halogen, cyano, $-C(O)C_{1-4}$alkyl, $C_{1-4}$alkyl, $C_{2-4}$alkenyl, $C_{2-4}$alkynyl, halo$C_{1-4}$alkyl, dihalo$C_{1-4}$alkyl and trihalo$C_{1-4}$alkyl;

$R^2$ is selected from the group consisting of halogen, $OR^A$, $N(R^B)_2$, $-C(O)C_{1-4}$alkyl optionally substituted with from 1 to 3 halogens, $-C(NH_2)=N-OH$, $-CO_2H$, $-CH_2-CO_2H$, $C_{1-6}$alkyl, $C_{2-6}$alkenyl, $C_{2-6}$alkynyl, halo$C_{1-4}$alkyl, dihalo$C_{1-4}$alkyl, trihalo$C_{1-4}$alkyl, halo$C_{1-4}$alkenyl, dihalo$C_{1-4}$alkenyl, trihalo$C_{1-4}$alkenyl, phenyl, and 5-6 membered heterocyclyl, wherein said phenyl or heterocyclyl group can either be unsubstituted or substituted by 1 to 3 substituents selected from the group consisting of $OR^A$, halogen, cyano, $-C(O)C_{1-4}$alkyl, $C_{1-4}$alkyl, $C_{2-4}$alkenyl, $C_{2-4}$alkynyl, halo$C_{1-4}$alkyl, dihalo$C_{1-4}$alkyl and trihalo$C_{1-4}$alkyl;

each of $R^3$, $R^4$, $R^5$ and $R^6$ is independently selected from the group consisting of hydrogen, $OR^A$, halogen, cyano, $C_{1-4}$alkyl, halo$C_{1-4}$alkyl, dihalo$C_{1-4}$alkyl, and trihalo$C_{1-4}$alkyl;

each $R^A$ is independently selected from the group consisting of hydrogen, $C_{1-4}$alkyl, $C_{2-4}$alkenyl, $C_{2-4}$alkynyl, $C_{3-6}$cycloalkyl, phenyl and benzyl; and each $R^B$ is independently selected from the group consisting of hydrogen and $C_{1-4}$alkyl.

More preferably in the compound of formula (III), $R^1$ is selected from the group consisting of $OR^A$, $N(R^B)_2$, $-C(O)C_{1-4}$alkyl, $C_{1-4}$alkyl, $C_{2-4}$alkenyl, $C_{2-4}$alkynyl, phenyl, and 5-6 membered heterocyclyl, wherein said phenyl or heterocyclyl group can either be unsubstituted or substituted by 1 to 3 substituents selected from halogen, cyano, $C_{1-4}$alkyl, $-C(O)C_{1-4}$alkyl, and $OR^A$;

each $R^A$ independently represents hydrogen or $C_{1-4}$alkyl; and each $R^B$ is independently selected from the group consisting of hydrogen and $C_{1-4}$alkyl. In such an embodiment preferably $R^2$ is selected from the group consisting of $-C(O)C_{1-4}$alkyl optionally substituted with from 1 to 3 halogens, $-C(NH_2)=N-OH$, $-CO_2H$, $-CH_2-CO_2H$, $C_{1-4}$alkyl, $C_{2-4}$alkenyl, $C_{2-4}$alkynyl, and 5-6 membered heterocyclyl wherein said heterocyclyl group can be either unsubstituted or substituted by 1 to 3 substituents selected from the group consisting of halogen, cyano, $-C(O)C_{1-4}$alkyl, $C_{1-4}$alkyl, $C_{2-4}$alkenyl, $C_{2-4}$alkynyl, halo$C_{1-4}$alkyl, dihalo$C_{1-4}$alkyl and trihalo$C_{1-4}$alkyl, and $OR^A$, in which $R^A$ represents hydrogen or $C_{1-4}$alkyl. More preferably $R^2$ is selected from the group consisting of $-C(O)CH_3$, $-C(NH_2)=N-OH$, $-CO_2H$, $-CH_2-CO_2H$, $C_{1-4}$alkyl, $C_{2-4}$alkenyl, $C_{2-4}$alkynyl, and 5-6 membered heterocyclyl wherein said heterocyclyl group can be either unsubstituted or substituted 1 to 3 substituents selected from halogen, cyano, $C_{1-4}$alkyl, $-C(O)C_{1-4}$alkyl, and $OR^A$ in which $R^A$ represents hydrogen or $C_{1-4}$alkyl.

In another preferred embodiment, in the compound of formula (III) $R^1$ is a 5-6 membered heterocyclyl group, wherein said heterocyclyl group is substituted with from 1 to 3 substituents selected from halogen, cyano and $C_{1-4}$alkyl; $R^2$ is selected from the group consisting of $-C(O)CH_3$, $-C(NH_2)=N-OH$, $-CO_2H$, and $-CH_2-CO_2H$; and each of $R^3$, $R^4$, $R^5$ and $R^6$ is independently selected from the group consisting of hydrogen and halogen.

In another preferred embodiment, in the compound of formula (III) $R^1$ is a 5-membered heterocyclyl group, wherein said heterocyclyl group is substituted with two substituents independently selected from methyl and ethyl; $R^2$ is $-C(NH_2)=N-OH$; and each of $R^3$, $R^4$, $R^5$ and $R^6$ is independently selected from the group consisting of hydrogen and halogen.

More preferably the ERβ agonist for use in the present invention is a compound having the formula:

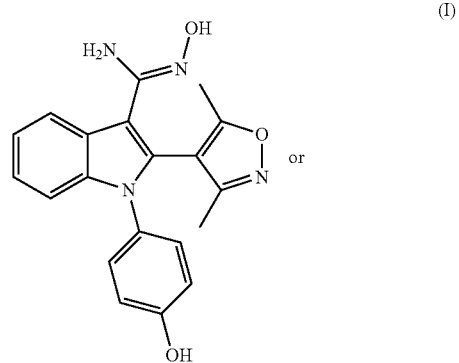

(I)

or

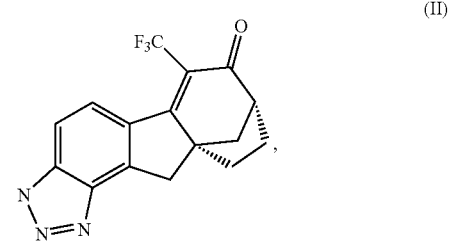

(II)

or a salt or an ester thereof. Most preferably the ERβ agonist is a compound of formula (I) ("Compound (I)") or a salt or an ester thereof.

ERβ agonists for use in the invention may be in the form of salts. Salts of compounds which are suitable for use in medicine are those wherein a counterion is pharmaceutically acceptable.

Suitable salts include those formed with organic or inorganic acids or bases. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)-alkyl- or aryl-sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine.

Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed.

Those skilled in the art of organic/medicinal chemistry will appreciate that many organic compounds can form complexes with solvents in which they are reacted or from which they are precipitated or crystallized. These complexes are known as "solvates". For example, a complex with water is known as a "hydrate". Solvates, such as hydrates, exist when the drug substance incorporates solvent, such as water, in the crystal lattice in either stoichiometric or non-stoichiometric amounts. Drug substances are routinely screened for the existence of hydrates since these may be encountered at any stage of the drug manufacturing process or upon storage of the drug substance or dosage form. Solvates are described in S. Byrn et al, Pharmaceutical Research 12(7), 1995, 954-954, and Water-Insoluble Drug Formulation, $2^{nd}$ ed. R. Liu, CRC Press, page 553, which are incorporated herein by reference. Accordingly, it will be understood by the skilled person that the ERβ agonists for use in the invention, as well as salts thereof, may therefore be present in the form of solvates. Solvates of compounds of the ERβ agonists of the invention which are suitable for use in medicine are those wherein the associated solvent is pharmaceutically acceptable. For example, a hydrate is an example of a pharmaceutically acceptable solvate.

Those skilled in the art of organic/medicinal chemistry will also appreciate that the ERβ agonist might be provided in the form of a prodrug. A prodrug may be defined as a compound which, upon administration to the recipient, is capable of being converted within the body, e. g. by hydrolysis in the blood, into its active form that has medical effects. Pharmaceutically acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference.

The active agents (the ERβ agonist and platinum-containing anti-cancer drug (plus any further therapeutic agent)) in the present invention may be administered by the same or different routes of administration.

The amount of the ERβ agonist which is required to achieve a therapeutic effect will vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician can readily determine and prescribe the effective amount of the drug required to prevent, counter or arrest the progress of the condition.

Oral dosages of the ERβ agonist of the present invention, when used for the indicated effects, will range between about 0.1 mg per kg of body weight per day (mg/kg/day) to about 5 mg/kg/day, preferably 0.3 to 3 mg/kg/day, more preferably 0.5 to 2.0 mg/kg/day, and most preferably 0.75 to 1.5 mg/kg/day for adult humans. An oral daily dosage therefore ranges from 5 mg to about 350 mg, preferably 20 mg to 200 mg, more preferably 35 mg to 150 mg, and most preferably from 50 mg to about 100 mg, for example 75 mg, for adult humans. Advantageously, an ERβ agonist for use in the present invention may be administered in a single daily dose, or the total daily dosage may be administered in divided doses of two, three or four times daily. For oral administration, the compositions are preferably provided in the form of tablets or other forms of presentation provided in discrete units containing from about 0.01 mg to about 500 mg of the active ingredient, preferably from about 1 mg to about 100 mg of active ingredient, for example 0.1, 0.5, 1.0, 2.5, 5.0, 10.0, 15.0, 25.0, 50.0, 100, or 500 milligrams of the active ingredient.

If intravenous dosing is used, a preferred dosing rate will be from about 0.1 to about 10 mg/kg/minute during a constant rate infusion. Typical infusion times are 5 to 90 minutes.

Pharmaceutical formulations of the ERβ agonist for use in this invention include those suitable for oral, parenteral (including subcutaneous, intradermal, intramuscular, intravenous [bolus or infusion], and intraarticular), inhalation (including fine particle dusts or mists which may be generated by means of various types of metered dose pressurized aerosol, nebulizers or insufflators), rectal, intraperitoneal and topical (including dermal, buccal, sublingual, and intraocular) administration.

The formulations of the ERβ agonist may conveniently be presented in unit dosage form and may be prepared by any of the methods well known in the art of pharmacy.

Formulations of the ERβ agonist suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations of the ERβ agonist are those containing an effective dose, as hereinbefore recited, or an appropriate fraction thereof, of the ERβ agonist.

It should be understood that in addition to the ingredients particularly mentioned above, the formulations for use in the invention may include other agents conventional in the art having regard to the type of formulation in question, for example those suitable for oral administration may include flavouring agents.

The Platinum-Containing Anti-Cancer Drug

Platinum-containing anti-cancer drugs are chemotherapeutic agents for the treatment of cancer that contain platinum. They are thought to cause crosslinking of DNA as monoadduct, interstrand crosslinks, intrastrand crosslinks or DNA protein crosslinks. They include, but are not limited to, cisplatin, carboplatin, oxaplatin, oxaliplatin, satraplatin, picoplatin, nedaplatin, triplatin, ormaplatin, tetraplatin, lipoplatin and phosphaplatins, for example cisplatin, carboplatin, oxaplatin, oxaliplatin, satraplatin, picoplatin, nedaplatin or triplatin, ormaplatin, tetraplatin and phosphaplatins. These compounds can be prepared by methods known in the art.

The platinum-containing anti-cancer drug for use in the present invention may be selected from the group consisting of cisplatin, carboplatin, oxaplatin, oxaliplatin, satraplatin, picoplatin, nedaplatin, triplatin, ormaplatin, tetraplatin, lipoplatin and phosphaplatins, for example cisplatin, carboplatin, oxaplatin, oxaliplatin, satraplatin, picoplatin, nedaplatin or triplatin, ormaplatin, tetraplatin and phosphaplatins. Preferably the platinum-containing anti-cancer drug is selected from the group consisting of cisplatin or carboplatin. Most preferably it is cisplatin.

The pharmaceutical formulation of the platinum-containing anti-cancer drug for use in the invention is, for example, a formulation for intravenous administration (especially in the case of cisplatin, carboplatin, and oxaliplatin) or oral administration (especially in the case of satraplatin).

The optimal dose of the platinum-containing anti-cancer drug depends on the dosing schedule, the potency of the particular drug chosen, the age, size, sex and condition of the patient, the nature and severity of the disease, and other relevant medical and physical factors. Thus, the pharmaceutically effective amount can be readily determined by the caregiver or clinician. Generally, an appropriate amount of platinum-containing anti-cancer drugs is chosen to obtain a chemotherapeutic effect. Intravenous doses of the platinum-containing anti-cancer drug in the present invention will typically contain from about 10 mg to about 500 mg of the active ingredient, preferably from about 50 mg to about 250 mg of active ingredient.

Platinum-containing anti-cancer drugs, such as cisplatin and carboplatin, are normally administered intravenously (IV). In such cases, they are administered over a period of about 10 to about 420 minutes, for example about 30 to about 300 minutes, for example about 30 to about 180 minutes, for example about 120 minutes. Where the platinum-containing anti-cancer drug is cisplatin, it is typically administered over about 120 minutes. For example, 75 mg/m$^2$ infused intravenously over about 120 minutes. A typical infusion rate is in the range from about 0.005 to about 0.05 mg/kg/minute. An effective intravenous dose of platinum-containing anti-cancer drug is typically from about 0.1 to about 50 mg/kg of body weight and preferably about 1 to about 5 mg/kg of body weight.

Oral doses of the platinum-containing anti-cancer drug in the present invention will range between about 1 mg per kg of body weight per day (mg/kg/day) to about 100 mg/kg/day, preferably 2 mg per kg of body weight per day (mg/kg/day) to 10 mg/kg/day, and most preferably 3 to 6 mg/kg/day, for adult humans.

The platinum-containing anti-cancer drug may be used, for example, in the amounts indicated in the Physicians' Desk Reference (PDR) or as otherwise determined by one of ordinary skill in the art. For example, a typical intravenous dosage of cisplatin for an adult is 70-100 mg/m$^2$ a day (corresponding to a dosage of about 125-185 mg a day), which may be repeated for up to 3 days. For example a typical single dose of cisplatin for an adult with malignant pleural mesothelioma is 75 mg/m$^2$ infused over 2 hours. The Standard of Care dosage of cisplatin for MPM is 75 mg/m$^2$ of cisplatin infused over 2 hours on day one of a 21 day cycle, followed by 20 days of rest with no further cisplatin being administered during that time. The cycle may be repeated one or several times depending on the stage of the MPM.

In one embodiment, a dosage regime of the present invention provides an ERβ agonist, for example Compound (I), and cisplatin, for use in the treatment of mesothelioma in a patient, for example for the treatment of MPM, wherein the ERβ agonist is administered in a dose of from 5 mg to about 350 mg, preferably 20 mg to 200 mg, more preferably 35 mg to 150 mg, and most preferably from 50 mg to 100 mg, for example 75 mg, and then after a time, t, of up to 24 hours, for example after 15 minutes, 30 minutes, 1 hour, 90 minutes, 2 hours, 4 hours, 8 hours, 16 hours or 24 hours, a dose of 75 mg/m$^2$ of cisplatin is infused over 2 hours on day 1 of a 21 day cycle, followed by 20 days of rest with no further cisplatin being administered during that time. Optionally, the ERβ agonist may also be administered on one or more days during the 21 day cycle after the administration of cisplatin, for example also on days 2 to 7 of the 21 day cycle, or also on days 2 to 21 of the 21 day cycle. The cycle may be repeated one or several times depending on the stage of the MPM.

When the platinum-containing anti-cancer drug is carboplatin, it is typically administered over about 30 minutes. A typical dose of carboplatin is from 2 to 8 target area under the plasma concentration-time curve (AUC), more typically 4 to 6 AUC infused intravenously over about 30 minutes. The units for the carboplatin AUC are mg carboplatin/mL·min. The exact dose of carboplatin may be calculated using the method of Calvert et al (Calvert, A. H., et al, J Clin Oncol (1989) 7: 1748-56). That method is: the carboplatin dose (in milligrams)=AUC×(globular filtration rate+25), i.e. if AUC=5, the carboplatin dose (in milligrams)=5×(globular filtration rate+25). Glomerular filtration rate is based on creatinine clearance, EDTA clearance, or the Cockcroft-Gault formula (as described in Cockcroft D, Gault M D. Nephron, 16:31-41, 1976; Winter, M. A., et al, Pharmacotherapy (2012) 32(7): 604/12; Brown, D. L., et al, Ann Pharmacother (2013) 47(7-8): 1039-44; or see available internet calculation tools based on the Cockcroft-Gault formula.

An example of a dose of carboplatin for an adult with malignant pleural mesothelioma is 4 to 6 AUC (for example 5 AUC) infused over 30 minutes on day one of a 21 day cycle, followed by 20 days of rest with no further carboplatin being administered during that time (see, for example, Santoro A., et al. J Thorac Oncol (2008) 3:756-63; Ceresoli G. L., et al. J Clin Oncol (2006) 24:1443). The cycle may be repeated one or several times depending on the stage of the MPM.

In one embodiment, a dosage regime of the present invention provides an ERβ agonist, for example Compound (I), and carboplatin, for use in the treatment of mesothelioma in a patient, for example for the treatment of MPM, wherein the ERβ agonist is administered in a dose of from 5 mg to about 350 mg, preferably 20 mg to 200 mg, more preferably 35 mg to 150 mg, and most preferably from 50 mg to 100 mg, for example 75 mg, and then after a time, t, of up to 24 hours, for example after 15 minutes, 30 minutes, 1 hour, 90 minutes, 2 hours, 4 hours, 8 hours, 16 hours or 24 hours, a dose of AUC 5 of carboplatin is infused over 30 minutes on day 1 of a 21 day cycle, followed by 20 days of rest with no further carboplatin being administered during that time. Optionally, the ERβ agonist may also be administered on one or more days during the 21 day cycle after the administration of carboplatin, for example also on days 2 to 7 of the 21 day cycle, or also on days 2 to 21 of the 21 day cycle. The cycle may be repeated one or several times depending on the stage of the MPM.

It should be understood that in addition to the ingredients particularly mentioned above, the formulations of this invention may include other agents conventional in the art having regard to the type of formulation in question, for example those suitable for oral administration may include flavouring agents.

Further Therapeutic Agents

Whilst an ERβ agonist and a platinum-containing anti-cancer drug may be used as the sole active agents in the treatment of the present invention, it is also possible for one or more further therapeutic agents to be used in combination with the ERβ agonist and platinum-containing anti-cancer drug. The one or more further therapeutic agent(s) may be used simultaneously, sequentially or separately from one or both of the ERβ agonist and the platinum-containing anti-cancer drug. Such further therapeutic agents may be a further ERβ agonist, or a different agent useful in the prevention or treatment of cancer, for example a chemotherapeutic agent.

In particular, the ERβ agonist and platinum-containing anti-cancer drug present invention can be used in combination with other agents useful for the treatment of mesotheliomas, for example pemetrexed. The individual components of such combinations can be administered separately at different times during the course of therapy or concurrently in divided or single combination forms.

In certain embodiments of the invention, for example, in embodiments where the platinum-containing anti-cancer drug is cisplatin, a further chemotherapeutic drug is administered. Preferably the further chemotherapeutic drug is pemetrexed. Pemetrexed may administered, for example, in the amounts indicated in the Physicians' Desk Reference (PDR) or as otherwise determined by one of ordinary skill in the art. For example, 500 mg/m$^2$ of pemetrexed administered as an intravenous infusion over 10 minutes on day 1 of a 21 day cycle along with cisplatin, the cisplatin being in a dose of 75 mg/m$^2$ infused over 2 hours beginning approximately 30 minutes after the end of the pemetrexed administration. This is followed by 20 days of rest with no further pemetrexed or cisplatin being administered during that time. The cycle may be repeated one or several times depending on the stage of the MPM. This is the Standard of Care for malignant pleural mesothelioma.

The standard of care using cisplatin and pemetrexed is described further in Vogelzang, N. J. et al. J Clin Oncol (2003) 21:2636. Apart from the further therapeutic agent pemetrexed, vitamin supplements may be administered 1 week before initial dose of pemetrexed until 21 days after last dose of pemetrexed (Folic acid 350-1000 mcg po qd; Vitamin B12 1000 mcg I.M. every 9 weeks). Dexamethasone (Decadron) 4 mg may also be administered twice daily the day before, the day of and the day after pemetrexed In certain embodiments of the invention, for example, in embodiments where the platinum-containing anti-cancer drug is carboplatin, a further chemotherapeutic drug is administered. Preferably the further chemotherapeutic drug is pemetrexed. For example, 500 mg/m$^2$ of pemetrexed is administered as an intravenous infusion over 10 minutes on day 1 of a 21 day cycle along with carboplatin, the carboplatin being in a dose of AUC 5 infused over 30 minutes beginning approximately 30 minutes after the end of the pemetrexed administration. This is followed by 20 days of rest with no further pemetrexed or carboplatin being administered during that time. The cycle may be repeated one or several times depending on the stage of the MPM. The treatment of mesothelioma using carboplatin and pemetrexed is described further in Ceresoli G. L., et al. J Clin Oncol (2006); 24:1443. Apart from the further therapeutic agent pemetrexed, vitamin supplements may be administered 1 week before initial dose of pemetrexed until 21 days after last dose of pemetrexed (Folic acid 350-1000 mcg po qd. Vitamin B12 1000 mcg I.M. every 9 weeks). Dexamethasone (Decadron) 4 mg may also be administered twice daily the day before, the day of and the day after pemetrexed.

In one embodiment, a dosage regime of the present invention provides an ERβ agonist, for example Compound (I), and cisplatin or carboplatin, and pemetrexed, for use in the treatment of mesothelioma in a patient, for example for the treatment of MPM, wherein the ERβ agonist is administered in a dose of from 5 mg to about 350 mg, preferably 20 mg to 200 mg, more preferably 35 mg to 150 mg, and most preferably from 50 mg to 100 mg, for example 75 mg, and then after a time, t, of up to 24 hours, for example after 15 minutes, 30 minutes, 1 hour, 90 minutes, 2 hours, 4 hours, 8 hours, 16 hours or 24 hours, a dose of 50 to 100 mg/m$^2$ (for example 75 mg/m$^2$) of cisplatin is infused over 2 hours or AUC 4 to 7.5 (for example 5 or 6) of carboplatin is infused is infused over 30 minutes, beginning approximately 30 minutes after administration of 500 mg/m$^2$ of pemetrexed as an intravenous infusion over 10 minutes, on day 1 of a 21 day cycle. This is followed by 20 days of rest with no further pemetrexed or cisplatin/carboplatin being administered during that time. Optionally, the ERβ agonist may also be administered on one or more days during the 21 day cycle after the administration of the cisplatin or carboplatin, for example also on days 2 to 7 of the 21 day cycle, or also on days 2 to 21 of the 21 day cycle. The cycle may be repeated one or several times depending on the stage of the MPM.

In one embodiment, a dosage regime of the present invention provides an ERβ agonist, for example Compound (I), and cisplatin and pemetrexed, for use in the treatment of mesothelioma in a patient, for example for the treatment of MPM, wherein the ERβ agonist is administered in a dose of from 5 mg to about 350 mg, preferably 20 mg to 200 mg, more preferably 35 mg to 150 mg, and most preferably from 50 mg to 100 mg, for example 75 mg, and then after a time, t, of up to 24 hours, for example after 15 minutes, 30 minutes, 1 hour, 90 minutes, 2 hours, 4 hours, 8 hours, 16 hours or 24 hours, a dose of 75 mg/m$^2$ of cisplatin is infused over 2 hours, beginning approximately 30 minutes after administration of 500 mg/m$^2$ of pemetrexed as an intravenous infusion over 10 minutes, on day 1 of a 21 day cycle. This is followed by 20 days of rest with no further pemetrexed or cisplatin being administered during that time. Optionally, the ERβ agonist may also be administered on one or more days during the 21 day cycle after the administration of cisplatin, for example also on days 2 to 7 of the 21 day cycle, or also on days 2 to 21 of the 21 day cycle. The cycle may be repeated one or several times depending on the stage of the MPM.

In one embodiment, a dosage regime of the present invention provides an ERβ agonist, for example Compound (I), and carboplatin and pemetrexed, for use in the treatment of mesothelioma in a patient, for example for the treatment of MPM, wherein the ERβ agonist is administered in a dose of from 5 mg to about 350 mg, preferably 20 mg to 200 mg, more preferably 35 mg to 150 mg, and most preferably from 50 mg to 100 mg, for example 75 mg, and then after a time, t, of up to 24 hours, for example after 15 minutes, 30 minutes, 1 hour, 90 minutes, 2 hours, 4 hours, 8 hours, 16 hours or 24 hours, a dose of 5 AUC of carboplatin is infused over 30 minutes, beginning approximately 30 minutes after administration of 500 mg/m$^2$ of pemetrexed as an intravenous infusion over 10 minutes, on day 1 of a 21 day cycle. This is followed by 20 days of rest with no further pemetrexed or carboplatin being administered during that time. Optionally, the ERβ agonist may also be administered on one or more days during the 21 day cycle after the administration of carboplatin, for example also on days 2 to 7 of the 21 day cycle, or also on days 2 to 21 of the 21 day cycle. The cycle may be repeated one or several times depending on the stage of the MPM.

In embodiments where the further chemotherapeutic drug is pemetrexed, dexamethasone may also be administered on the day before, the day of, and the day after pemetrexed administration. To reduce toxicity, patients treated with pemetrexed may also be instructed to take a low-dose oral folic acid preparation or a multivitamin with folic acid on a daily basis. For example, folic acid 400 mcg to 1000 mcg may be administered orally once daily beginning 7 days before the first dose of pemetrexed and continuing during the full course of therapy and for 21 days after the last dose of pemetrexed. Patients may also receive one intramuscular injection of vitamin B12 during the week preceding the first dose of pemetrexed and every 3 cycles thereafter. Subsequent vitamin B12 injections may be given on the same day as pemetrexed. Therefore, in embodiments of the invention where the treatment comprises administration of the further chemotherapeutic drug pemetrexed, the treatment may further comprise administration of one or more of: dexamethasone; folic acid preparation; a multivitamin with folic acid; and vitamin B12.

The above other therapeutic agents, may be used, for example, in those amounts indicated in the Physicians' Desk Reference (PDR) or as otherwise determined by one of ordinary skill in the art.

Other treatments for mesothelioma may be used in combination with the present invention, for example radiotherapy. The treatment of the present invention may be used in addition to surgery for example pleurectomy/decortication (P/D) or extrapleural pneumonectomy (EPP) to remove tumour, or thoracentesis/paracentesis or pleurodesis if fluid build-up in the chest or abdomen.

A further ERβ agonist for use as an additional agent in the present invention may be a compound described as an ERβ agonist in any one of WO 2002/072561, WO 03/044006, WO 2004/094401, WO 2006/08871, WO 2006/019831, WO 2006/044176, WO 2006/062876, WO 2007/062876, EP 2143432, WO 2008/033894, WO 2008/043567, WO 2009/012191, WO 2009/012954, WO 2009/055734, WO 2009/124968, WO 2009/127686, WO 2010/031852, WO2 011/042473, WO 2011/042474, WO 2011/042475, WO 2011/042477 and WO 2013/017619.

Further chemotherapeutic agents for use in the present invention may be selected from the group consisting of a further platinum-containing anti-cancer drug (for example selected from the group consisting of cisplatin, carboplatin, oxaplatin, oxaliplatin, satraplatin, picoplatin, nedaplatin and triplatin); alkylating agents (for example nitrogen mustards (including echlorethamine, cyclophosphamide, melphalan, chlorambucil, ifosfamide and busulfan), nitrosoureas (including nitrosoureas include n-nitroso-n-methylurea (MNU), carmustine (BCNU), lomustine (CCNU) and semustine (MeCCNU), fotemustine and streptozotocin), tetrazines (including dacarbazine, mitozolomide and temozolomide), aziridines (including thiotepa, mytomycin and diaziquone (AZQ)), and non-classical alkylating agents (including procarbazine and hexamethylmelamine)); anti-metabolites (for example anti-folates (including pemetrexed and methotrexate), fluoropyrimidines (including fluorouracil and capecitabine), deoxynucleoside analogues (including cytarabine, gemcitabine, decitabine, vidaza, fludarabine, nelarabine, cladribine, clofarabine and pentostatin) and thiopurines (including thioguanine and mercaptopurine)); anti-microtubule agents (for example vinca alkaloids (including vincristine, vinblastine, vinorelbine, vindesine and vinflunine) and taxanes (including paclitaxel, etoposide and teniposide)); topoisomerase inhibitors (for example irinotecan, topotecan, doxorubicin, mitoxantrone, novobiocin, merbarone, and aclarubicin); other enzyme inhibitors (for example bortezomib, imatinib and procarbazine); and cytotoxic antibiotics (for example anthracyclines (including oxorubicin, daunorubicin, epirubicin, idarubicin, pirarubicin, aclarubicin and mitoxantrone) and actinomycin, bleomycin, plicamycin and mitomycin)).

Mesothelioma

The term "mesothelioma" as used herein includes but is not limited to epithelioid, sarcomatoid, and mixed (biphasic) mesothelioma. Types of mesothelioma include, but are not limited to, pleural, peritoneal, pericardial and tunica vaginalis malignant mesothelioma.

The treatment of the present invention is useful for the treatment of mesothelioma, for example epithelioid, sarcomatoid (fibrous), and mixed (biphasic) mesotheliomas. The treatment of the present invention is particularly useful for the treatment of epithelioid and mixed mesotheliomas. The treatment of the present invention is useful for the treatment of, for example, malignant pleural, malignant peritoneal, malignant pericardial or malignant tunica vaginalis mesothelioma. The treatment of the present invention is particularly useful for the treatment of malignant pleural mesothelioma.

As used herein, a "patient" refers to any mammal (e.g., a human), that may be susceptible to mesothelioma. The compounds for use of the present invention find particular use for the treatment of a human patient.

Time, t

In the treatment of the invention, the ERβ agonist is administered to the patient first, and then after a time, t, of up to 24 hours, the platinum-containing anti-cancer drug is administered.

In certain preferred embodiments, t is up to about 16 hours; preferably up to about 8 hours; more preferably up to about 4 hours; most preferably up to about 2 hours.

In certain preferred embodiments, t is from about 15 minutes to about 24 hours; from about 15 minutes to about 16 hours; preferably from about 30 minutes to about 8 hours; more preferably from about 30 minutes to about 4 hours; more preferably from about 1 hour to about 2 hours; most preferably about 2 hours.

In embodiments which comprise administering the ERβ agonist, platinum-containing anti-cancer drug and pemetrexed, preferably at least the platinum-containing anti-cancer drug is administered up to about 24 hours after the administration of the ERβ agonist. In more preferred embodiments, at least the platinum-containing anti-cancer drug is administered from up to about 4 hours after the administration of the ERβ agonist, and most preferably up to about 2 hours after the administration of the ERβ agonist. In such embodiments, it is preferable to administer the pemetrexed before the platinum-containing anti-cancer drug, for example from about 10 to about 60 minutes before, and more preferably about 30 minutes before. Preferably the platinum-containing anti-cancer drug is cisplatin or carboplatin.

In embodiments which comprise administering the ERβ agonist and both cisplatin and pemetrexed, preferably at least the cisplatin is administered up to about 24 hours after the administration of the ERβ agonist. In more preferred embodiments, at least the cisplatin is administered from up to about 4 hours after the administration of the ERβ agonist, and most preferably up to about 2 hours after the administration of the ERβ agonist. In such embodiments, it is preferable to administer the pemetrexed before the cisplatin, for example from about 10 to about 60 minutes before, and more preferably about 30 minutes before.

In embodiments which comprise administering the ERβ agonist and both cisplatin and pemetrexed, preferably at least the cisplatin is administered from about 15 minutes to about 24 hours after the administration of the ERβ agonist. In more preferred embodiments, at least the cisplatin is administered from about 30 minutes to about 4 hours after the administration of the ERβ agonist, and most preferably at about 2 hours after the administration of the ERβ agonist.

In embodiments which comprise administering the ERβ agonist and both carboplatin and pemetrexed, preferably at least the carboplatin is administered up to about 24 hours after the administration of the ERβ agonist. In more preferred embodiments, at least the carboplatin is administered from up to about 4 hours after the administration of the ERβ agonist, and most preferably up to about 2 hours after the administration of the ERβ agonist. In such embodiments, it is preferable to administer the pemetrexed before the carboplatin, for example from about 10 to about 60 minutes before, and more preferably about 30 minutes before.

In embodiments which comprise administering the ERβ agonist and both carboplatin and pemetrexed, preferably at least the carboplatin is administered from about 15 minutes to about 24 hours after the administration of the ERβ agonist. In more preferred embodiments, at least the carboplatin is administered from about 30 minutes to about 4 hours after the administration of the ERβ agonist, and most preferably at about 2 hours after the administration of the ERβ agonist.

In certain preferred embodiments the ERβ agonist is Compound (I), the platinum-containing anti-cancer drug is cisplatin, and t is, for example, up to 8 hours, up to 4 hours, up to two hours, or about 2 hours, and optionally pemetrexed is also administered.

In another embodiment the ERβ agonist is Compound (I), the platinum-containing anti-cancer drug is carboplatin, and t is, for example, up to 8 hours, up to 4 hours, up to two hours, or about 2 hours, and optionally pemetrexed is also administered.

In certain preferred embodiments, the ERβ agonist is administered to the patient first, and then after a time, t, of up to 24 hours, for example up to about 16 hours; up to about 8 hours; up to about 4 hours; or about 2 hours, the platinum-containing anti-cancer drug is administered, and optionally pemetrexed is administered, and following this, one or more further doses of ERβ agonist are administered on one or more days after the platinum-containing anti-cancer drug is administered. For example, the ERβ agonist may be administered daily for up to and including 20 days after the platinum-containing anti-cancer drug.

In certain preferred embodiments, the ERβ agonist is administered to the patient first, and then after a time, t, of between 15 minutes and 24 hours, for example between 30 minutes and 16 hours; between 30 minutes and 8 hours; between 1 hour and 4 hours; or about 2 hours, the platinum-containing anti-cancer drug is administered, and optionally pemetrexed is administered, and following this, one or more further doses of ERβ agonist are administered on one or more days after the platinum-containing anti-cancer drug is administered. For example, the ERβ agonist may be administered daily for up to and including 20 days after the platinum-containing anti-cancer drug.

EXAMPLES

The following materials and methods are applicable to one or more of the examples below.

Materials and Methods

Reagents and Antibodies

The monoclonal antibodies specific for α-tubulin, PARP1 and the polyclonal antibody specific for ERβ were purchased from Santa Cruz Biotechnology (Santa Cruz, Calif., USA). Phospho-AKT (pSer473) was from Cell Signaling Technology (Beverly, Mass., USA), anti-mouse and antirabbit IgG peroxidase conjugated antibodies and chemical reagents were from Sigma-Aldrich (St Louis, Mo., USA). ECL was from Amersham Pharmacia Biotech (Uppsala, Sweden). Nitrocellulose membranes and protein assay kit were from Bio-Rad (Hercules, Calif., USA). Culture media, sera, antibiotics and LipofectAMINE transfection reagent were from Invitrogen (Carlsbad, Calif., USA). The ERβ selective agonist Compound (I) can be prepared as described in WO 2009/127686. Cisplatin was from EBEWE Arzneimittel Ges.m.h.H (Unterach, Austria) or EBEWE Italia SRL (Roma, Italy). Pemetrexed was from Eli Lilly (Houten, the Netherlands).

Cell Cultures and Transfection

The epithelioid MPM derived REN cell line was isolated, characterized and provided by Dr. Albelda S. M. (University of Pennsylvania, Philadelphia; PA, USA). The biphasic MSTO-211H and the mesothelial MET5A cell lines were obtained from the Istituto Scientifico Tumori (IST) Cellbank, Genoa, Italy; the MMB and MMP cell lines have been derived from pleural effusions of patients with MPM and stabilized in culture (Cacciotti P, et al., Proc Natl Acad Sci USA 2001; 98:12032-7; Pinton G., et al, Cancer Res 2009; 69:4598-604); the H2596 cell line was produced by Dr. H. I. Pass from surgical specimens derived from patients with resected MPM (Pass H. I., et al., Ann Thorac Surg 1995; 59(4):835-44). Cells were grown in RPMI medium supplemented with 10% FBS, 100 m/ml streptomycin and 10 μg/ml penicillin at 37° C. in a humidified environment containing 5% CO2. $Mycoplasma$ infection was excluded by the use of $Mycoplasma$ Plus™ PCR Primer Set kit from Stratagene (La Jolla, Calif., USA). For MSTO-211H/ERβ cells, cells grown to 80% confluence in tissue culture dishes were transiently transfected with the pCNX2 plasmid expressing human wild type ERβ (Addgene, Cambridge, Mass., USA) using LipofectAMINE reagent as described by the manufacturer. Gene silencing was achieved using an ERβ-specific shRNA lentiviral plasmid (pLKO.1-puro) by Sigma (St Louis, Mo., USA) or specific siRNAs by Qiagen (Hilden, Germany).

Proliferation Assays

Cells were seeded at a density of $10 \times 10^4$ cells/well in 6-well plates in RPMI medium supplemented with 10% FBS, 100 μg/ml streptomycin and 10 μg/ml penicillin and incubated over-night at 37° C. in a humidified environment containing 5% $CO_2$ to allow adherence. Following treatment cells were trypsinized and stained with Trypan blue. The number of cells considered viable (unstained cells) was counted in a Bürker haemocytometer within 5 minutes after staining.

Wash-Off Experiments

Cell cultures were pretreated with Compound (I) for 1-16 hours (depending on experiment) followed by wash-off and then replenished with normal growth medium±cisplatin, pemetrexed or cisplatin/pemetrexed. Total incubation time was 24-72 hours (depending on experiment). Control cultures were maintained in normal growth medium without added drug. The number of viable cells was determined as described for the proliferation assay.

Add-on Experiments

In the add-on experiments the second drug was added directly to the cell culture medium without wash-off of the first drug. Total incubation time was 24 hours. Control cultures were maintained in normal growth medium without added drug. The number of viable cells was determined as described for the proliferation assay.

Cell Lysis and Immunoblot

Cells were extracted with 1% NP-40 lysis buffer (1% NP-40, 150 mM NaCl, 50 mM Tris-HCl pH 8.5 mM EDTA, 10 mM NaF, 10 mM $Na_4P_2O_7$, 0.4 mM $Na_3VO_4$) with freshly added protease inhibitors (10 μg/ml leupeptin, 4 μg/ml pepstatin and 0.1 Unit/ml aprotinin). For protein extraction from tissues, ~100 mg of each sample were homogenized, using a Potter-Elvehjem homogenizer device, in 1% NP-40 lysis buffer. Lysates were centrifuged at 13.000×g for 10 minutes at 4° C. and the supernatants were collected and assayed for protein concentration with the Bio-Rad protein assay method.

Proteins were separated by SDS-PAGE under reducing conditions. Following SDS-PAGE, proteins were transferred to nitrocellulose, reacted with specific antibodies and then detected with peroxidase-conjugate secondary antibodies and chemioluminescent ECL reagent. Densitometric analysis was performed using the GS 250 Molecular Image (Bio-Rad).

Cell Cycle Analysis

For cell cycle/apoptosis analysis, $5 \times 10^5$ cells were seeded in tissue culture plates and treated with 100 μM cisplatin for 24 hours or pre-treated for 2 hours with 10 nM Compound (I) followed by wash-off and continued growth in normal medium±100 μM cisplatin, for additional 24 hours at 37° C. in a 5% $CO_2$ atmosphere. After incubation, detached and suspended cells were harvested in complete RPMI and centrifuged at 500×g for 10 minutes. Pellets were washed with PBS, fixed in ice-cold 75% ethanol at 4° C., treated with 100 mg/mL RNAse A for 1 hour at 37° C., stained with 25 μg/mL propidium iodide and finally analyzed by using a flow cytometer FACS (Becton Dickinson, San Jose, Calif., USA) and Modfit software (Verity Software House, Topsham, Me., USA).

In Vivo Experiments

Animals. CD1 nude mice (males, 6 weeks old; Charles River, Calco, Italy) received intraperitoneal (i.p.) injections of $2 \times 10^6$ luciferase transduced REN cells in 0.5 mL of RPMI medium. After anesthetization and i.p. injections of 0.3 mL of 15 mg/mL D-luciferin, tumor dimension and localization of luminescent cells was monitored using the In Vivo Imaging System (IVIS) series (Xenogen Corporation, Hopkinton, Mass., USA). Regions of interest were identified around the tumor sites and were quantified as total photon counts using Living Image software (Xenogen Corporation). The values of tumor sizes were obtained, subtracting luminescence signals of each weekly measurement by the average of all animals within a treatment group on the 15th day after inoculation (day when treatment started). To evaluate treatment toxicity, mice were weighed at the start and end of treatments. Mice were killed and necropsied after 20 days of treatment. In vivo experiments were approved by Istituto Scientifico Tumori (Genoa, Italy) ethical committee and conform to the relevant regulatory standards. Mice were maintained and handled under aseptic conditions, and were allowed access to food and water ad libitum.

Drug Administration. An elapse of 15 days was allowed for the formation of detectable tumor nodules by IVIS imaging. Mice were then weighed and stratified into treatment groups of ten animals. Treatment protocols were done from the 15th day to the 35th day, and mice were analyzed weekly by IVIS imaging to assess tumor growth. One dose of Compound (I) was used (10 mg/kg/day). Compound (I) was dissolved in the vehicle (5% DMSO/40% PEG 400/55% water) and administrated once daily (days 1-21) by subcutaneous administration. 5 mg/kg cisplatin solution (EBEWE Italia srl, Roma, Italy) was administrated subcutaneously at day 4 and 11, respectively, and 150 mg/kg pemetrexed (dissolved in isotonic saline) (Eli Lilly, Houten, Nederland) was injected subcutaneously days 5-9 and 12-16, respectively. Untreated animals were dosed with empty vehicle. At day 35 mice from the four groups were euthanized and necropsied. Tumors growing in the peritoneum were excised, and one part of the tumor tissues was immediately frozen and stored at −80° C. for later analysis.

Statistical Analysis

Statistical evaluation of the differential analysis was performed by one way ANOVA and Student's t-test. The threshold for statistical significance was set at $p \leq 0.05$. The statistical analysis of in vivo experiments was done by using R Core Team. R: A language and environment for statistical computing. R Foundation for Statistical Computing, Vienna, Austria, 2012 ISBN 3-900051-07-0. To compare different groups the non-parametric Kruskal-Wallis test was used; if differences were found significant ($p \leq 0.05$) the Wilkoxon rank sum test was subsequently applied to do pair wise comparisons.

Example 1

The Effect of Compound (I) on MPM Cell Proliferation (a) The growth inhibitory effect of different doses of Compound (I) (range 1-100 nM) was tested on ERβ positive REN mesothelioma cells using the proliferation assay described above. The results are shown in FIG. 1A. Compound (I) significantly ($p \leq 0.05$) reduced cell growth and viability in a dose-dependent manner, with highest efficacy at 10 nM.

Figure 1B:
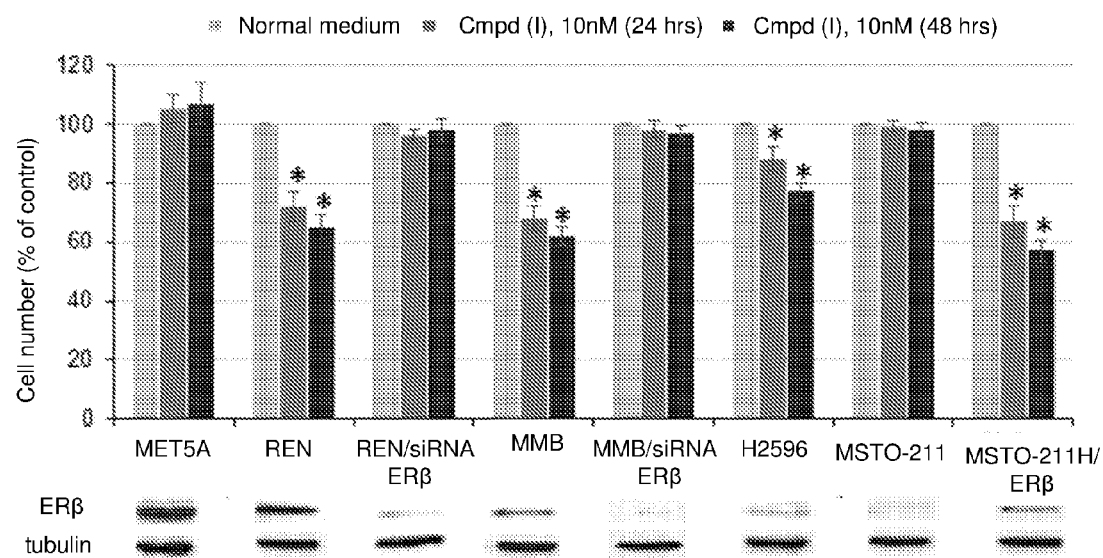
FIG. 1B shows the percentage of growth inhibition after 24 and 48 hours treatment with Compound (I) (10 nM) in mesothelium derived cells (MET5A) and in MPM derived cells with different levels of endogenous ERβ expression (REN, MMB, H2596 and MSTO-211H) and MSTO-211H cells transfected with an ERβ expression vector (MSTO-211H/ERβ). Also shown are REN and MMB cells in which ERβ has been knocked down with ERβ specific siRNA (REN/siRNA ERβ and MMB/siRNA ERβ). The Western blots below the bar graphs show ERβ protein expression for each cell line and the loading control tubulin. Each bar represents mean+/−s.d; *p≤0.05.

(b) The anti-proliferative activity of Compound (I) (10 nM) as single agent at 24 and 48 hours was assessed in the non-malignant mesothelial MET5A cells, the malignant mesothelioma cells REN, MMB, H2596 and MSTO-211H; MSTO-211H cells transiently transfected to express human ERβ (MSTO-211H/ERβ); and the malignant mesothelioma cells REN and MMB in which ERβ has been knocked down with ERβ specific siRNA (REN/siRNA ERβ and MMB/siRNA ERβ). The results are shown in FIG. 1B.

Compound (I) significantly ($p \leq 0.05$) inhibited proliferation of the REN and MMB cells, whereas no inhibitory effect was observed in the MET5A cells, despite high endogenous levels of ERβ. This may relate to their non-malignant phenotype. The H2596 cells had a weak response to Compound (I), as H2596 cells express very low levels of ERβ. The ERβ negative MSTO-211H cells showed no response to Compound (I) treatment. However, transient transfection of the MSTO-211H cells with an ERβ expression vector sensitized these cells to Compound (I).

Example 2

Figures 2A, 2B:
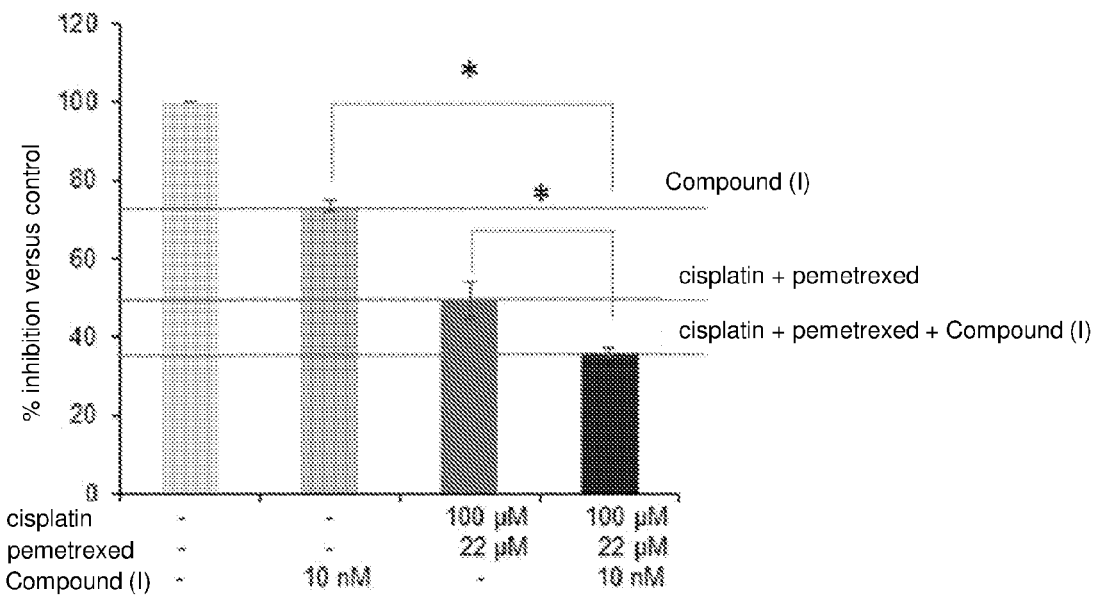
FIG. 2A shows REN cell viability after 24 hour exposure to Compound (I) (10 nM) alone or in combination with cisplatin (100 μM) and pemetrexed (22 μM), versus untreated cells. Each bar represents mean+/−s.d; *p≤0.05.
FIG. 2B shows the treatment schedule of the in vivo experiment.

The Effect of Compound (I) on the Effectiveness of Cisplatin/Pemetrexed In Vitro and In Vivo (a) The growth inhibitory effect of adding Compound (I) (10 nM) to the cisplatin/pemetrexed chemo combination (at their respective $IC_{50}$ concentrations) was studied in REN cells, compared to normal medium (control), Compound (I) only and cisplatin/pemetrexed. The number of viable cells was determined as described for the proliferation assay. Cell viability after 24 hours was measured. The results are shown in FIG. 2A.

The triple combination of Compound (I)/cisplatin/pemetrexed (10 nM/100 μM/22 μM, respectively) was superior to either Compound (I) alone or cisplatin/pemetrexed treatment alone, demonstrating that Compound (I) enhances the effect of cisplatin/pemetrexed treatment.

Figure 2C:
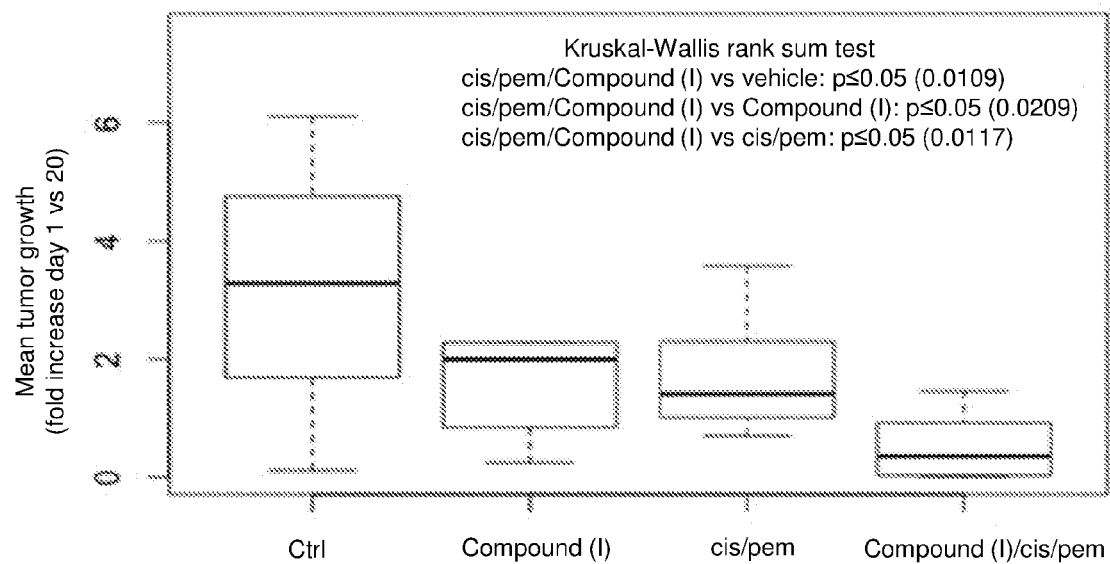
FIGS. 2C and 2D show box plots of the 4 different treatment groups showing in vivo mean tumor growth (FIG. 2C) and mean tumor growth inhibition (FIG. 2D) evaluated at 21 days of treatment. The thick segments represent the medians while the upper and lower borders of each rectangle represent the quartiles. Bars show minimum and maximum values for each group, and outliers are identified by a small circle.
Figure 2D:
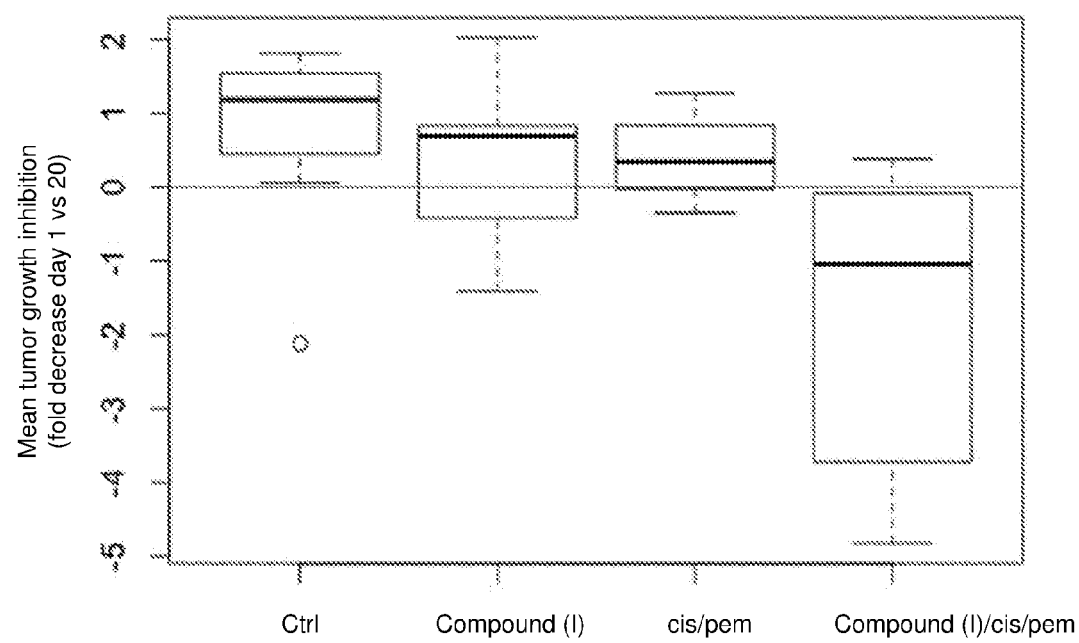

(b) The effect of Compound (I) on the cisplatin/pemetrexed combination was also evaluated in a mesothelioma in vivo mouse model. Six weeks old CD1 nude male mice were inoculated intra peritoneum with $2 \times 10^6$ REN cells (4 groups, 10 animals per group). Prior to inoculation, the MPM cells were transduced with a lentiviral vector carrying the luciferase gene, to allow imaging in live mice. Treatments with vehicle, Compound (I), cisplatin/pemetrexed or Compound (I)/cisplatin/pemetrexed were initiated at day 15 (when tumor incidence in the peritoneal cavity was 100% in all animal groups) and continued for 21 days as indicated in FIG. 2B. Compound (I) was administered by subcutaneous injection at 10 mg/kg/day. Untreated animals were subcutaneously dosed with empty vehicle. Two groups were treated at day 4 and 11 with 5 mg/kg cisplatin followed by 5 days treatment with 150 mg/kg pemetrexed (days 5-9 and 12-16), alone or in combination with Compound (I). At day 35 mice were sacrificed and tumors were dissected and immediately frozen. The results are shown in FIGS. 2C and 2D.

Mice treated with Compound (I) produced a similar decrease in tumor dimensions as the cisplatin/pemetrexed treated group, compared to vehicle controls within 10 days (data not shown). After 20 days of treatment a statistically significant reduction in tumor growth was observed in the group treated with Compound (I)/cisplatin/pemetrexed as compared to the vehicle, Compound (I), and cisplatin/pemetrexed groups. Therefore, treatment with Compound (I) in combination with cisplatin/pemetrexed in vivo had greater efficacy than either treatment alone, and caused a significantly reduced tumor load compared to vehicle treated animals at the end of the treatment period. Further, the triple combination of Compound (I)/cisplatin/pemetrexed shrunk the tumor volume even below the tumor volume at the start of treatment. Treatment with Compound (I) was not to be toxic, as assessed by monitoring changes of mice body weights during drug administration. Therefore, the growth inhibitory effects shown in vitro in Example 2(a) translated into anti-tumorigenic activity in vivo in mice.

Example 3

Figure 3A:
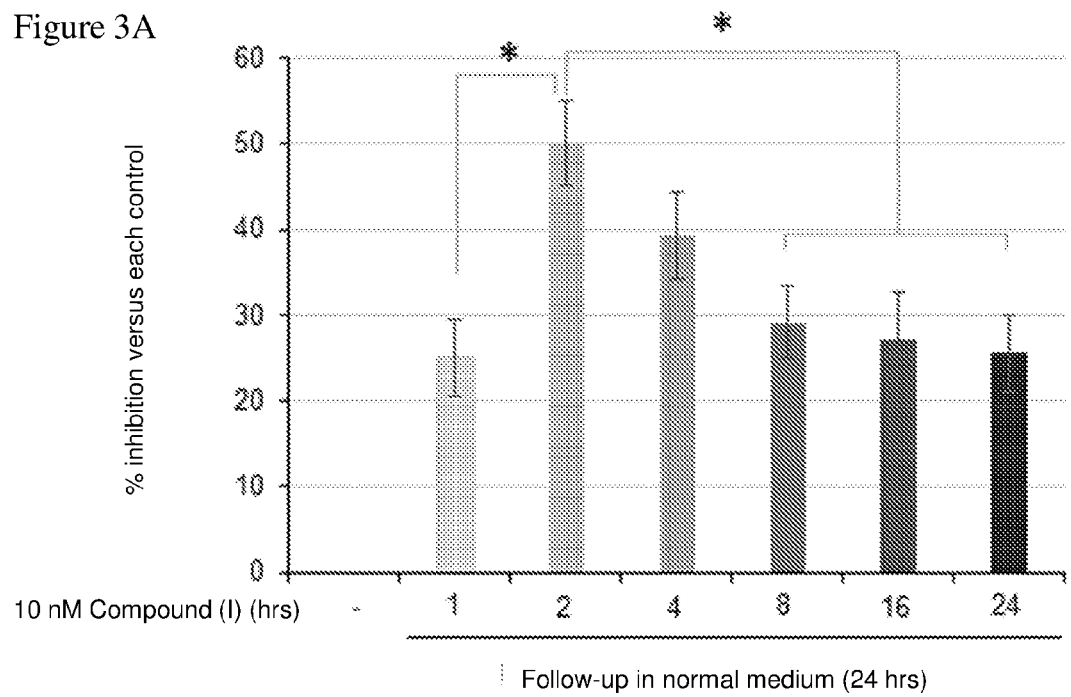
FIG. 3A shows the percentage of growth inhibition in REN cells after 1, 2, 4, 8, 16 or 24 hours pre-treatment with Compound (I) (10 nM) followed by wash-off and continued growth in normal medium for an additional 24 hours. Each bar represents mean+/−s.d; *p≤0.05.

The Effect of Compound (I) on Growth of REN Cells (a) The growth inhibitory effect of brief exposure to Compound (I) (10 nM) (1, 2, 4, 8, 16 and 24 hours) was studied in REN cells. Cell cultures were pretreated with Compound (I) for 1-16 hours followed by wash-off and then replenished with normal growth medium. Total incubation time was 24 hours. For the 24 hour study, cells were maintained in culture with Compound (I) for 24 hours incubation time. Control cultures were maintained in normal growth medium. The number of viable cells was determined as described for the proliferation assay. The results are shown in FIG. 3A.

Exposure to Compound (I) for 2 hours presented significantly ($p \leq 0.05$) increased growth inhibitory activity relative to 1 hour exposure and exposures longer than 8 hours.

Figure 3B:
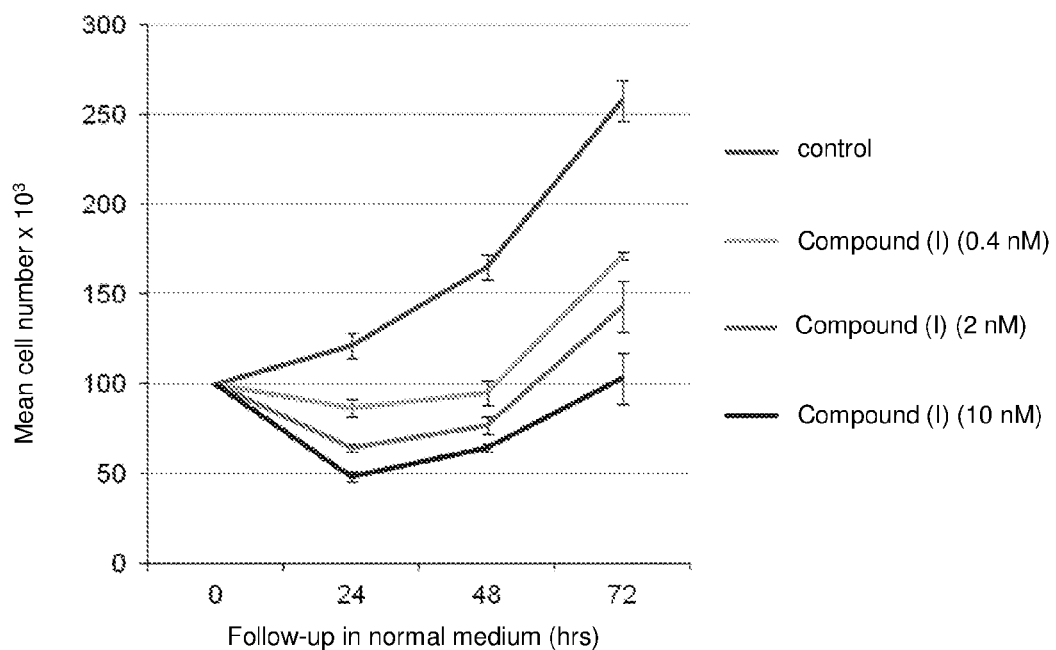
FIG. 3B shows REN cell viability after preexposure for 2 hours to normal medium (control) or Compound (I) (10 nM) followed by wash-off and continued growth for an additional 24, 48 or 72 hours in normal medium.

(b) The growth inhibitory effect over 72 hours after brief exposure to varying doses of Compound (I) (0.4, 2 and 10 nM) for 2 hours was studied in REN cells. Cell cultures were pretreated with different concentrations of Compound (I) (0.4, 2 and 10 nM) for 2 hours followed by wash-off and then continued growth in normal medium (without Compound (I)) for an additional 24, 48 or 72 hours. Control cultures were maintained in normal growth medium only. The number of viable cells was determined as described for the proliferation assay at 0, 24, 48 and 72 hours. The results are shown in FIG. 3B.

The duration of inhibitory effect on REN cell proliferation sustained for at least 24 hours irrespective of concentration of Compound (I) used in the 2-hours pre-treatment period. The largest anti-proliferative effect was observed with the highest Compound (I) concentration used. After 24 hours the cells slowly regained proliferative activity and from 48 hours post Compound (I) pre-treatment, their proliferative rates were similar to that of REN cells cultivated in normal medium from the start of the study.

Example 4

Figure 4A:
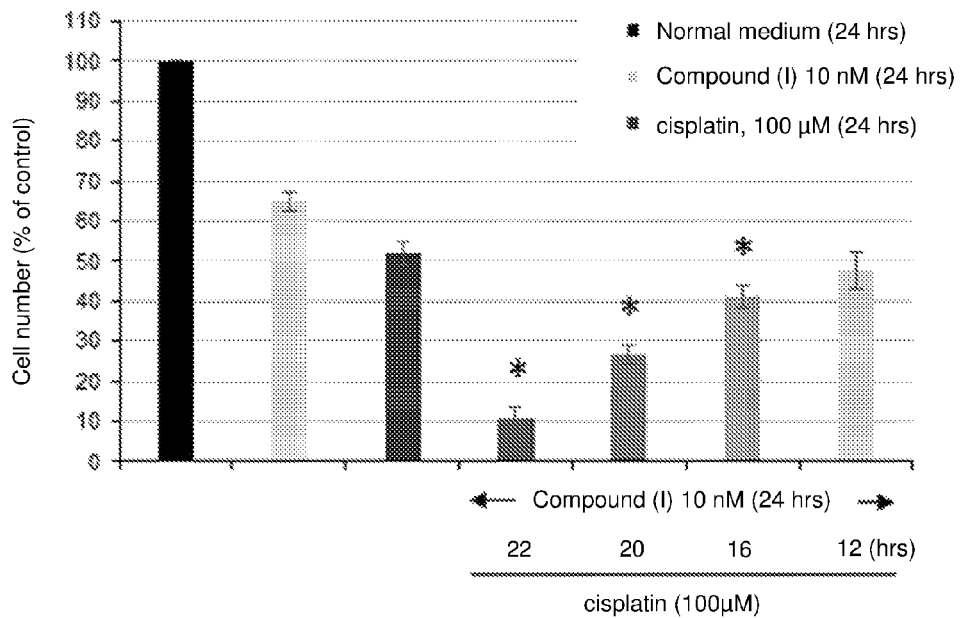
FIG. 4A shows the effect on REN cell viability of adding cisplatin (100 μM) 2, 4, 8 or 12 hours after start of Compound (I) (10 nM) treatment. Each bar represents mean+/−s.d; *p≤0.05.

The Effect of Pre-Treatment with Compound (I) on the Effect of Cisplatin and/or Pemetrexed on REN Cells (a) 100 µM cisplatin was added to REN cell cultures pre-treated for 2, 4, 8, and 12 hours with 10 nM Compound (I) (add on experiment). The number of viable cells at 24 hours was determined as described for the proliferation assay above. Control cultures were maintained in normal growth medium; growth medium plus Compound (I) (10 nM); and growth medium plus cisplatin (100 µM). The results are shown in FIG. 4A.

The enhanced anti-proliferative effect of cisplatin was time-dependent with the greatest inhibitory effect obtained when adding cisplatin after 2 hours of Compound (I) pre-treatment.

Figure 4B:
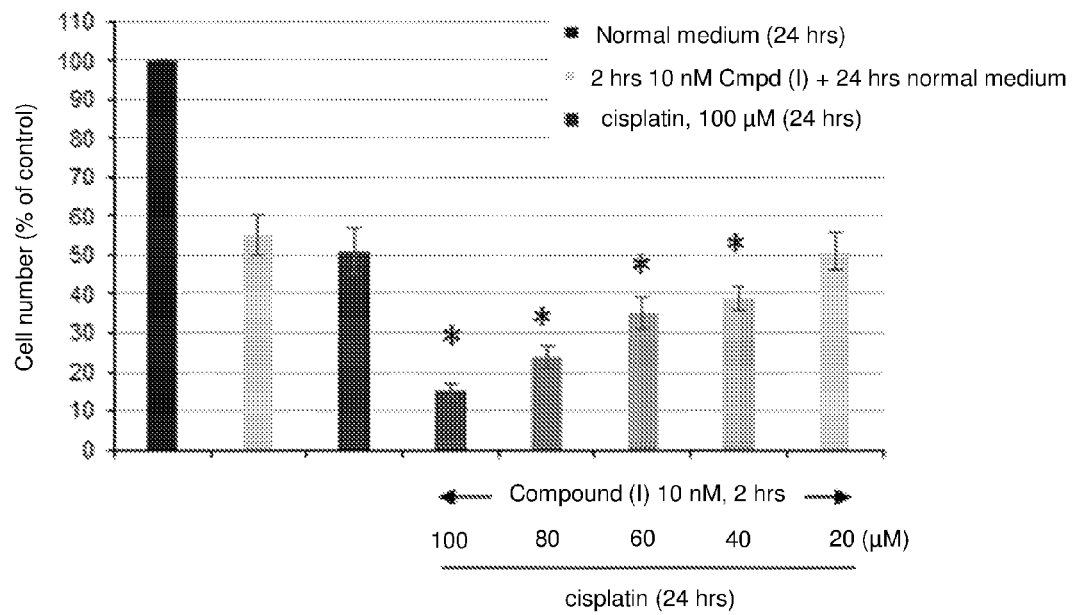
FIG. 4B shows REN cell viability after 2 hours pre-treatment with Compound (I) (10 nM) followed by wash-off and continued growth in normal medium supplemented with different concentrations of cisplatin (20-100 μM), for an additional 24 hours. Each bar represents mean+/−s.d; *p≤0.05.

(b) Different concentrations of cisplatin (20, 40, 60, 80 and 100 µM) were added to REN cell cultures pre-treated for 2 hours with Compound (I) (10 nM). Cells were pre-treated with Compound (I) (10 nM) for 2 hours followed by wash-off and continued growth in normal medium supplemented with different concentrations of cisplatin (20, 40, 60, 80 and 100 µM), for an additional 24 hours. The number of viable cells after the additional 24 hours was determined as described for the proliferation assay above. Control cultures were maintained in normal growth medium; 2 hours Compound (I) (10 nM), wash-off and then continued growth in normal medium for an additional 24 hours; and growth medium plus cisplatin (100 µM). The results are shown in FIG. 4B.

The most efficacious anti-proliferative effect was observed when Compound (I) pre-treatment was combined with the highest concentration of cisplatin (100 µM). However, surprisingly, 2 hours pre-treatment with Compound (I) in combination with 20 µM cisplatin was as efficacious as 100 µM cisplatin alone.

Figure 4C:
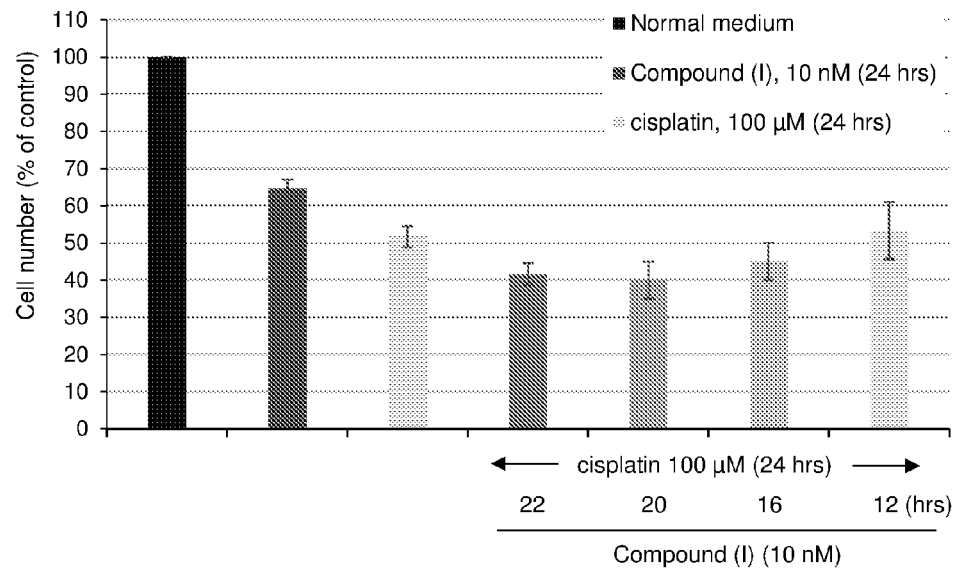
FIG. 4C shows the effect on REN cell viability of adding Compound (I) (10 nM) 2, 4, 8 or 12 hours after start of cisplatin treatment (100 μM). Each bar represents mean+/−s.d.
Figure 4D:
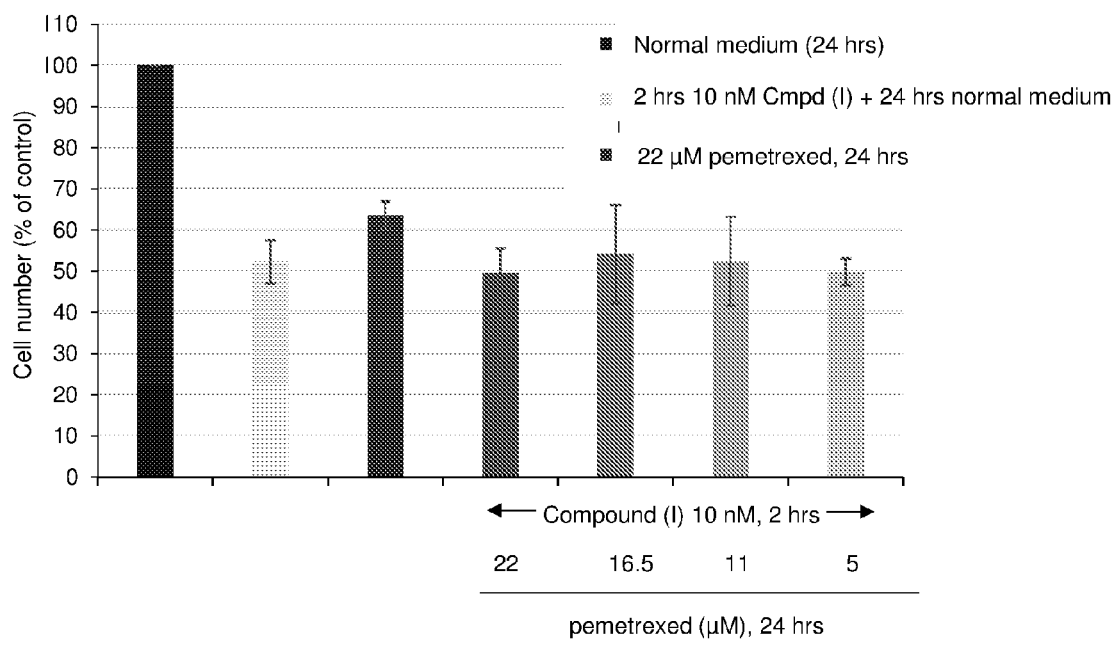
FIG. 4D shows REN cell viability after 2 hours pre-treatment with Compound (I) (10 nM) followed by wash-off and continued growth in normal medium supplemented with different concentrations of pemetrexed (5-22 μM), for an additional 24 hours. Each bar represents mean+/−s.d.
Figure 4E:
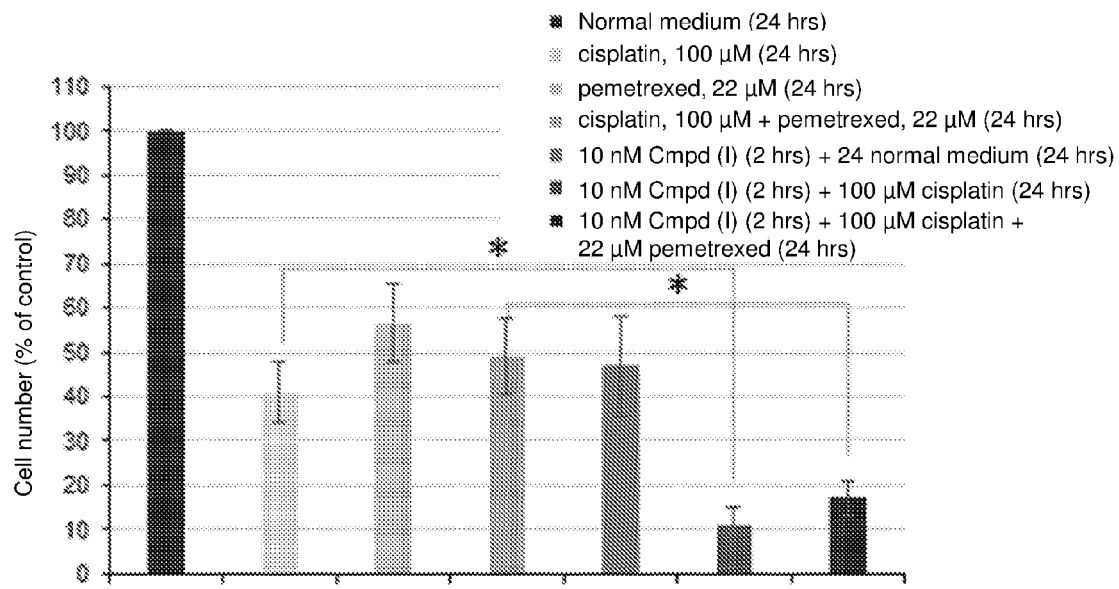
FIG. 4E shows REN cell viability after 2 hours pre-treatment with Compound (I) (10 nM) followed by wash-off and continued growth in normal medium or medium containing cisplatin (100 μM), pemetrexed (22 μM) or the cisplatin (100 μM)/pemetrexed (22 μM) combination, for an additional 24 hours. Each bar represents mean+/−s.d; *p≤0.05.
Figure 4F:
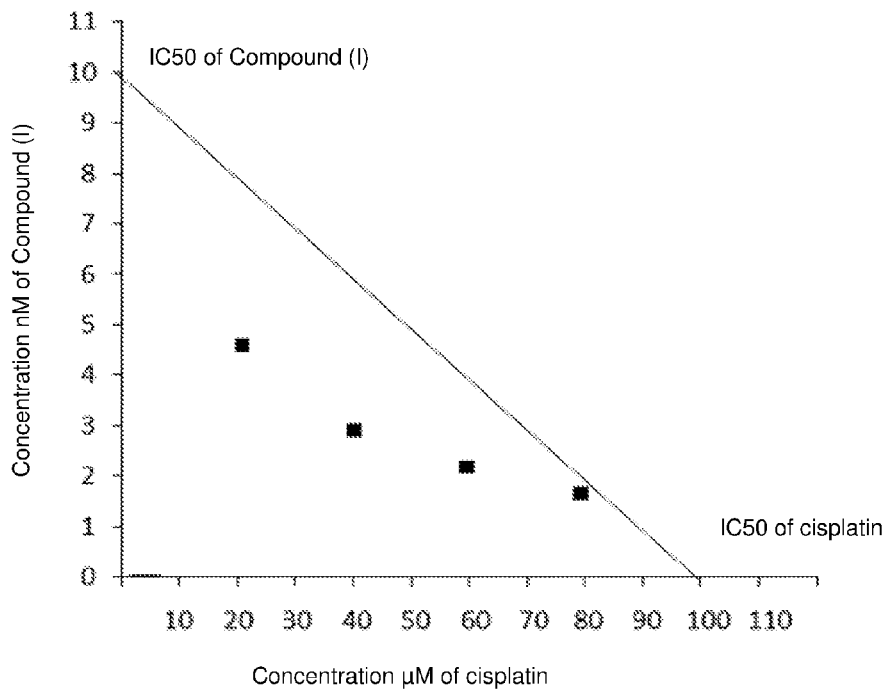
FIG. 4F shows the results of an isobologram analysis of the results shown in FIG. 4B.

An isobologram analysis of the results of this experiment was carried out (Tallarida R J., Perspectives in Pharmacology 2001; 298(3):865-72; Tallarida R J., Perspectives in Pharmacology 2006; 319:1-7). The results are shown in FIG. 4F. As can be seen from that figure, the combination of Compound (I) and cisplatin has a synergistic effect.

(c) Compound (I) (10 nM) was added to REN cell cultures pre-treated with cisplatin for 2, 4, 8 and 12 hours with 100 µM cisplatin (add on experiment). The number of viable cells at 24 hours was determined as described for the proliferation assay above. Control cultures were maintained in normal growth medium; growth medium plus Compound (I) (10 nM); and growth medium plus cisplatin (100 µM). The results are shown in FIG. 4C.

Whilst cells treated with both cisplatin and Compound (I) showed greater growth inhibition than cells treated with only one of the agents, the pretreatment with cisplatin prior to adding Compound (I) did not result in synergistic inhibition of cell growth and viability. This is in contrast to pre-treatment with Compound (I) before adding cisplatin, as shown in Example 4(a). Therefore, synergistic inhibition of malignant mesothelioma cell proliferation and survival by Compound (I) and cisplatin only occurs with Compound (I) pretreatment, and not in the reverse order.

(d) Different doses of pemetrexed (5, 11, 16.5 and 22 µM) were added to REN cell cultures pre-treated for 2 hours with Compound (I) (10 nM). Cells were pre-treated with Compound (I) (10 nM) for 2 hours followed by wash-off and continued growth in normal medium supplemented with different concentrations of pemetrexed (5, 11, 16.5 and 22 µM) for an additional 24 hours. The number of viable cells after the additional 24 hours was determined as described for the proliferation assay above. Control cultures were maintained in normal growth medium; 2 hours Compound (I) (10 nM), wash-off and then continued growth in normal medium for an additional 24 hours; and growth medium plus pemetrexed (22 µM). The results are shown in FIG. 4D.

No enhanced anti-proliferative effect was obtained when adding pemetrexed after 2 hours of Compound (I) pre-treatment. This is in contrast to pre-treatment with Compound (I) before adding cisplatin, as shown in Example 4a. Therefore, pretreatment with Compound (I) does not exhibit the same beneficial synergistic effect on pemetrexed as it does on cisplatin.

(e) Cisplatin (100 µM) or cisplatin (100 µM) and pemetrexed (22 µM) were added to REN cell cultures pre-treated with Compound (I) (10 nM) for 2 hours. Cells were pre-treated with Compound (I) (10 nM) for 2 hours followed by wash-off and continued growth in normal medium supplemented with cisplatin (100 µM), or cisplatin (100 µM) and pemetrexed (22 µM), for an additional 24 hours. The number of viable cells after the additional 24 hours was determined as described for the proliferation assay above. Control cultures were maintained in normal growth medium; growth medium plus cisplatin (100 µM); growth medium plus pemetrexed (22 µM); growth medium plus cisplatin (100 µM) and pemetrexed (22 µM); and 2 hours pre-treatment with Compound (I) (10 nM) followed by wash-off and continued growth in normal medium, for an additional 24 hours. The results are shown in FIG. 4E.

Pre-treatment of REN cells with Compound (I) before the addition of cisplatin or cisplatin/pemetrexed resulted in a strong synergistic inhibitory effect on cell growth and viability.

Example 5

Cell-Cycle Analysis of Cells Treated with Compound (I)

REN cells were treated for 24 hours with 100 µM cisplatin or pre-treated 2 hours with 10 nM Compound (I) followed by wash-off and continued growth in normal medium±100 µM cisplatin, for an additional 24 hours. Cell cycle analysis was performed as described above. Control cultures were maintained in normal growth medium. After treatments, cells were stained with propidium iodide and analysed for cellular DNA content by flow cytometry. The results are shown in FIG. 5A.

Pre-treatment with Compound (I) for 2 hours followed by 24 hours cisplatin treatment resulted in significant and efficient blockage of the cell cycle in the G0/G1 phase and inhibition of cells entering the S-phase of the cell cycle compared to any other treatment. Moreover, a significant higher percentage of dead cells were found in wells pre-treated with Compound (I) followed by cisplatin compared to other treatment regimens tested.

One plausible explanation for the higher number of dead cells in the Compound (I)/cisplatin treated cells was induction of apoptosis.

Figure 5B:
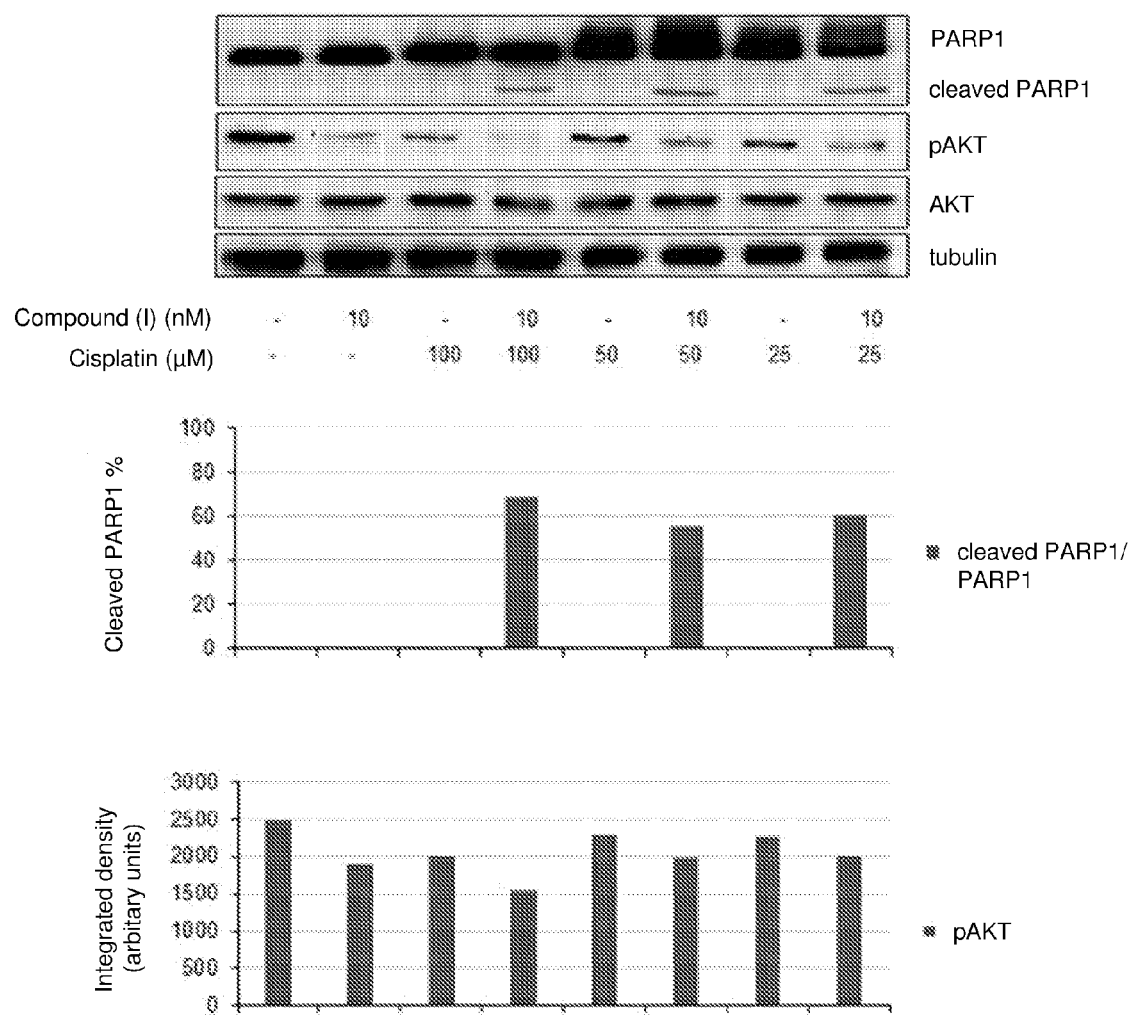
FIG. 5B shows Western blot analysis and relative densitometry of PARP1 cleavage and AKT phosphorylation in REN cells treated for 24 hours with cisplatin (25, 50 and 100 μM) or pre-treated 2 hours with Compound (I) (10 nM) followed by wash-off and continued growth in normal medium±cisplatin (25, 50 and 100 μM), for an additional 24 hours. Total AKT and Tubulin staining were used for normalization.

Levels of PARP1, cleaved PARP1, AKT and phosphorylated AKT in REN cells treated for 24 hours with cisplatin (25, 50 and 100 µM) or pre-treated 2 hours with Compound (I) (10 nM) followed by wash-off and continued growth in normal medium±cisplatin (25, 50 and 100 µM), for an additional 24 hours were also determined by Western blot analysis and relative densitometry. Total AKT and Tubulin staining were used for normalization. The results are shown in FIG. 5B. PARP1 cleavage was analysed as it is an indicator of apoptotic cell death. As increased AKT activity has been implicated in the control of proliferation, apoptosis and cisplatin resistance (Pinton G., et al, PLoS One (2012) 7:e36856), AKT activation status following different treatments was also analysed.

As expected from the cell cycle analysis and percentage of dead cells, 2 hours Compound (I) treatment, prior to addition of cisplatin, had the greatest effect on the appearance of cleaved PARP1 (FIG. 5B). Interestingly, neither cisplatin nor Compound (I) alone resulted in significant PARP1 cleavage. Compound (I) treatment also significantly reduced AKT phosphorylation both in the absence and in the presence of cisplatin (FIG. 5B).

Example 6

Effect of Compound (I) on Cisplatin Toxicity in MET5A Cells

Figure 6A:
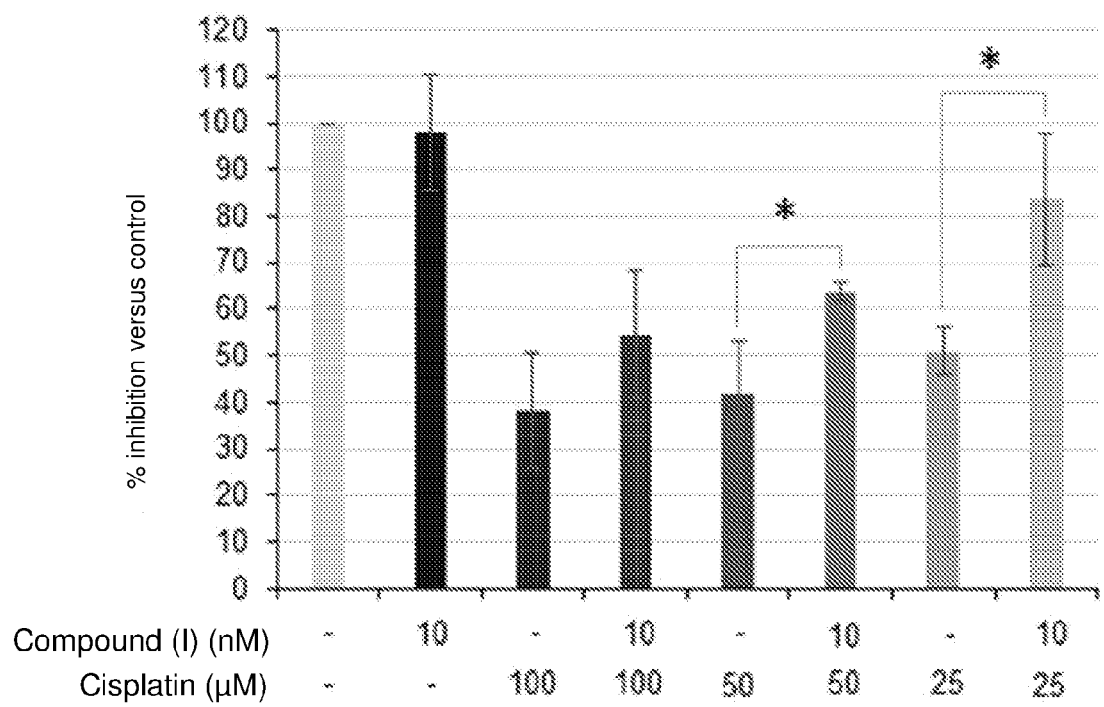
FIG. 6A shows the effect on MET5A cell viability after 24 hours treatment with cisplatin (25, 50 and 100 μM) or 2 hours pre-treatment with Compound (I) (10 nM) followed by wash-off and continued growth in normal medium±different concentrations of cisplatin (25, 50 and 100 μM), for an additional 24 hours. Each bar represents mean+/−s.d; *p≤0.05.

The effect of Compound (I) on cisplatin toxicity was tested in the normal mesothelium derived cell line MET5A. MET5A cells were treated with 10 nM Compound (I) for 2 hours followed by wash-off and continued growth in normal medium or in the presence of varying doses of cisplatin (25, 50, 100 µM) for an additional 24 hours. Control cultures were maintained in normal growth medium; growth medium plus cisplatin (100 µM); and 2 hours Compound (I) (10 nM), wash-off and then continued growth in normal medium for an additional 24 hours. The results are shown in FIG. 6A.

MET5A cells showed higher sensitivity to cisplatin treatment than REN cells, with an IC$_{50}$ of 25 µM. Compound (I) alone had no effect on MET5A cell proliferation or viability. A protective effect was observed when Compound (I) pre-treatment was combined with low doses of cisplatin.

Therefore, in contrast to the effect in the malignant REN cells where Compound (I) significantly increased cell toxicity to cisplatin (see Example 4(a), (b) and (e)), Compound (I) diminished and/or counteracted the toxicity of cisplatin in the non-malignant mesothelial MET5A cells. It appears that the ERβ agonist acts as a rheostat, trying to re-establish homeostasis in diseased or stressed cells.

Levels of PARP1, cleaved PARP1, AKT and phosphorylated AKT in the MET5A cell cultures at 24 hours were also determined by Western blot analysis and relative densitometry.

Figure 6B:
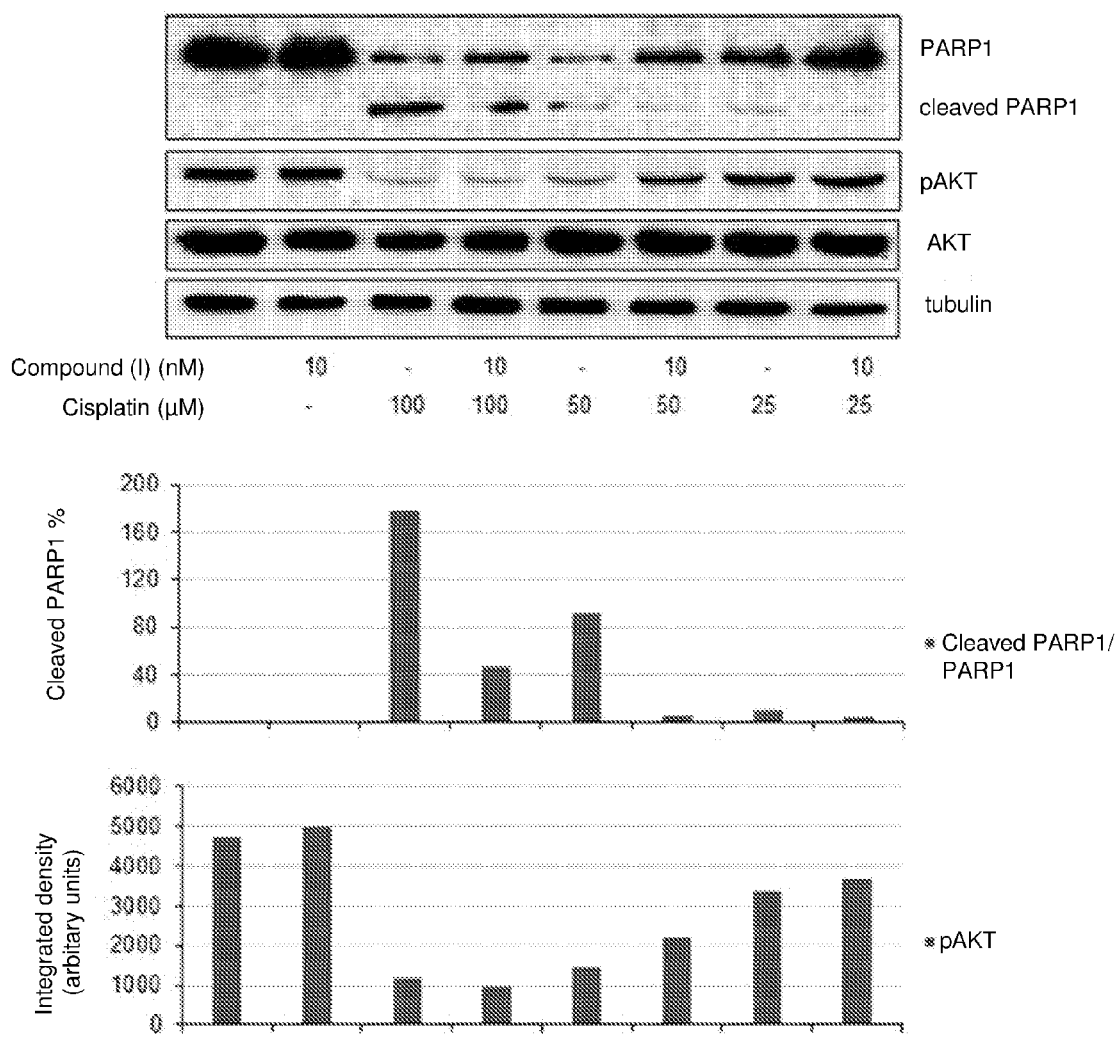
FIG. 6B shows Western blot analysis and relative densitometry of PARP1 cleavage and AKT phosphorylation in MET5A cells treated with cisplatin (25, 50 and 100 μM) for 24 hours or pre-treated for 2 hours with Compound (I) (10 nM) followed by wash-off and continued growth in normal medium±different concentrations of cisplatin (25, 50 and 100 μM), for an additional 24 hours. Total AKT and Tubulin staining were used for normalization.

Compound (I) pre-treatment reduced the percentage of cleaved PARP1 in cells exposed to all concentrations of cisplatin (see FIG. 6B), in accordance with data obtained on cell viability (FIG. 6A). Compound (I) had no effect on basal pAKT levels in the MET5A control cells but it antagonized the cisplatin-mediated inhibition of pAKT (also shown in FIG. 6B). AKT pathway activation is associated with anti-apoptotic effects and cell survival. Together with the effects of Compound (I) on reduced PARP1 cleavage, this may explain the Compound (I)-mediated decrease in cisplatin cytotoxicity in the non-malignant MET5A cells.

Example 7

The Effect of Pre-Treatment with Compound (I) and Cisplatin on MMP Cells

Figure 7A:
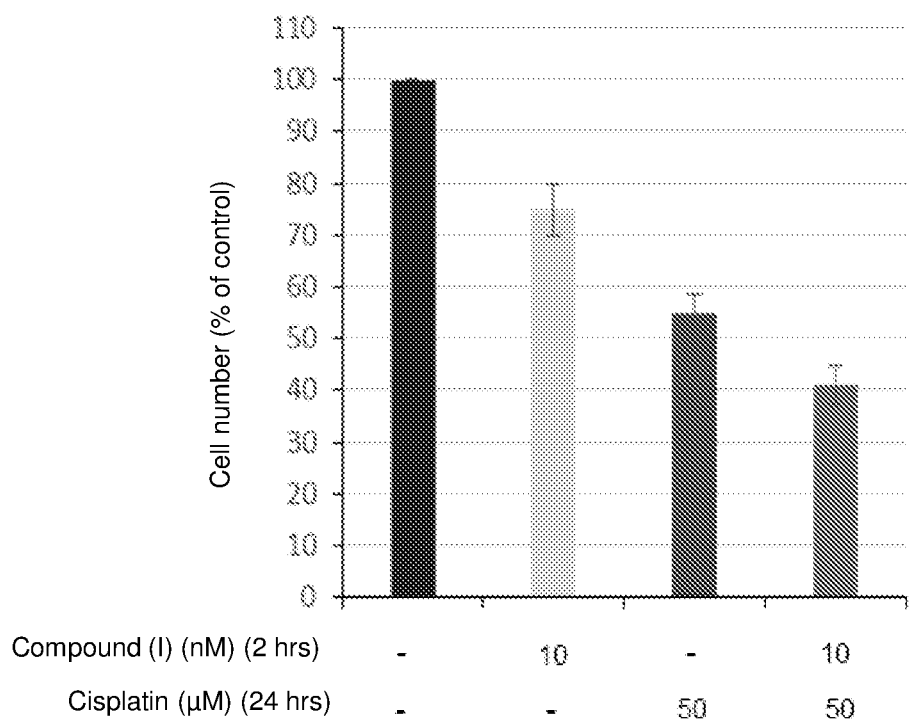
FIG. 7A shows MMP cell viability after treatment with cisplatin (50 μM) for 24 hours or pre-treated for 2 hours with Compound (I) (10 nM) followed by wash-off and continued growth in normal medium±cisplatin (50 μM), for an additional 24 hours. Each bar represents mean+/−s.d.

50 µM cisplatin was added to MMP cell cultures pre-treated for 2 hours with 10 nM Compound (I) (wash-off experiment). The number of viable cells at 24 hours was determined as described for the proliferation assay above. Control cultures were maintained in normal growth medium; growth medium plus Compound (I) (10 nM); and growth medium plus cisplatin (50 µM). The results are shown in FIG. 7A.

An enhanced anti-proliferative effect of cisplatin was observed when the cells were pre-treated for 2 hours with Compound (I).

Levels of PARP1, cleaved PARP1, AKT and phosphorylated AKT in the MMP cell cultures at 24 hours were also determined by Western blot analysis.

Figure 7B:
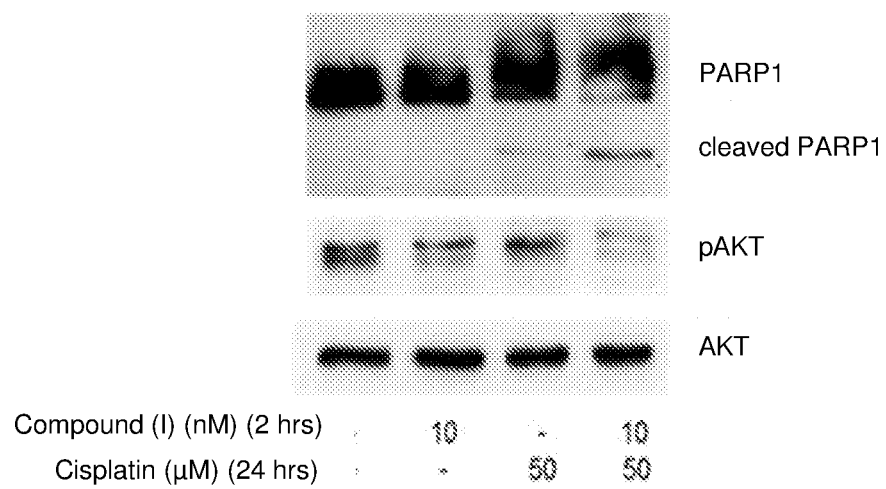
FIG. 7B shows Western blot analysis of PARP1 cleavage and AKT phosphorylation in MMP cells treated with cisplatin (50 μM) for 24 hours or pre-treated for 2 hours with Compound (I) (10 nM) followed by wash-off and continued growth in normal medium±cisplatin (50 μM), for an additional 24 hours.

The results are shown in FIG. 7B. As can be seen from that figure, there was the most significant increase in the level of cleaved PARP1 in the cells that were pre-treated for two hours with Compound (I) followed by wash-off and continued growth in normal medium supplemented with 50 µM cisplatin. Compound (I) treatment significantly reduced AKT phosphorylation both in the absence and in the presence of cisplatin, but most significantly when the cells were treated with Compound (I) and cisplatin.

Therefore, in a second human malignant mesothelioma cell line, MMP, Compound (I) in combination with cisplatin resulted in synergistic growth inhibition compared to Compound (I) or cisplatin alone in vitro. Moreover, similar to the effect in REN cells, the combination of Compound (I) and cisplatin in the MMP cells decreased the level of phosphorylated AKT and increased the levels of cleaved PARP1.

The invention claimed is:

1. A kit comprising a platinum-containing anti-cancer drug and an ERβ agonist.

2. A kit comprising a platinum-containing anti-cancer drug and an ERβ agonist as claimed in claim 1, wherein the ERβ agonist is a compound having the formula:

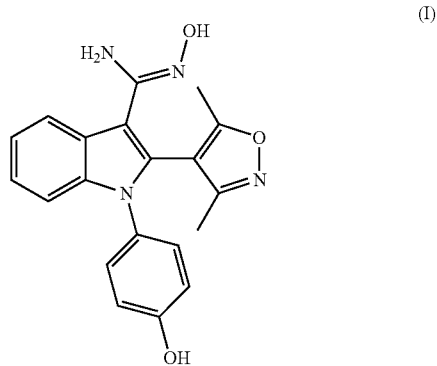 [SMILES: Cc1noc(C)c1-c1c(/C(N)=N/O)c2ccccc2n1-c1ccc(O)cc1]

(I)

or a salt or an ester thereof, and
the platinum-containing anti-cancer drug is cisplatin.

3. A kit as claimed in claim 1, wherein the ERβ agonist is a compound of formula (III) or a salt or an ester thereof,

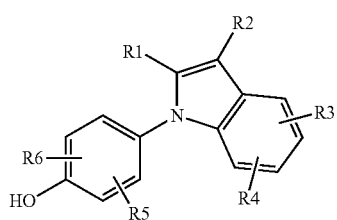

(III)

wherein $R^1$ is selected from the group consisting of halogen, cyano, nitro, $OR^A$, $N(R^B)_2$, —C(O)$C_{1-4}$alkyl, —SO$_2$$C_{1-4}$alkyl, $C_{1-6}$alkyl, $C_{2-6}$alkenyl, $C_{2-6}$alkynyl, halo$C_{1-6}$alkyl, dihalo$C_{1-6}$alkyl, trihalo$C_{1-6}$alkyl, halo$C_{2-6}$alkenyl, dihalo$C_{2-6}$alkenyl, trihalo$C_{2-6}$alkenyl, cyano$C_{1-6}$alkyl, $C_{1-4}$alkoxy$C_{1-6}$ alkyl, $C_{3-8}$cycloalkyl, $C_{3-8}$cycloalkyl$C_{1-6}$ alkyl, phenyl, benzyl, and 5-10 membered heterocyclyl, wherein said phenyl, benzyl or heterocyclyl group can be either unsubstituted or substituted with from 1 to 3 substituents, each substituent being selected from the group consisting of $OR^A$, halogen, cyano, nitro, —C(O)$C_{1-4}$alkyl, $C_{1-6}$alkyl, $C_{2-6}$alkenyl, $C_{2-6}$alkynyl, halo$C_{1-6}$ alkyl, dihalo$C_{1-6}$ alkyl and trihalo$C_{1-6}$alkyl;

$R^2$ is selected from the group consisting of halogen, cyano, nitro, $OR^A$, $N(R^B)_2$, N(OH)$_2$, —C(O)$C_{1-4}$alkyl optionally substituted with from 1 to 3 halogens, —SO$_2$$C_{1-4}$alkyl, —C(O)NH—OH, —C(NH$_2$)=N—OH, —C(CO$_2$H)=N—OH, —C(NH$_2$)=NH, —C(NH $C_{1-4}$alkyl)=NH, —C(O—$C_{1-4}$alkyl)=NH, —C(NH$_2$)=N—NH$_2$, —NH—C(NH$_2$)=NH, —NH—C(O)NH$_2$, —N=C(—NH—CH$_2$CH$_2$—NH—), —S—CN, —S—C(NH$_2$)=NH, —S—C(NH$_2$)=N—OH, —CO$_2$H, —CH$_2$—CO$_2$H, —CH(OH)CO$_2$H, —C(O)CO$_2$H, SO$_3$H, CH$_2$SO$_3$H, $C_{1-6}$alkyl, halo$C_{1-6}$alkyl, dihalo$C_{1-6}$alkyl, trihalo$C_{1-6}$alkyl, cyano$C_{1-6}$alkyl, $C_{1-4}$alkoxy$C_{1-6}$ alkyl, $C_{2-6}$alkenyl, $C_{2-6}$alkynyl, $C_{3-8}$cycloalkyl, $C_{3-8}$cycloalkyl$C_{1-6}$alkyl, phenyl, benzyl and 5-10 membered heterocyclyl wherein said phenyl, benzyl or heterocyclyl group can be either unsubstituted or substituted with from 1 to 3 substituents each substituent being selected from the group consisting of $OR^A$, halogen, cyano, nitro, $C_{1-6}$alkyl, $C_{2-6}$alkenyl, $C_{2-6}$alkynyl, halo$C_{1-6}$alkyl, dihalo$C_{1-6}$alkyl and trihalo$C_{1-6}$ alkyl; provided that if one of $R^1$ and $R^2$ represents halogen, the other must represent a group other than halogen;

each of $R^3$, $R^4$, $R^5$ and $R^6$ is independently selected from the group consisting of hydrogen, $OR^A$, halogen, cyano, nitro, $C_{1-6}$alkyl, $C_{2-6}$alkenyl, $C_{2-6}$alkynyl, halo$C_{1-6}$alkyl, dihalo$C_{1-6}$alkyl and trihalo$C_{1-6}$alkyl;

each $R^A$ is independently selected from the group consisting of hydrogen, $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, $C_{6-10}$aryl and $C_{6-10}$aryl$C_{1-6}$alkyl, each optionally substituted by from 1 to 3 halogen atoms; and each $R^B$ is independently selected from the group consisting of hydrogen, $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, $C_{6-10}$aryl and $C_{6-10}$aryl$C_{1-6}$alkyl, each optionally substituted by from 1 to 3 halogen atoms;

with the proviso that the compound of formula (III) is not
4-[3-(4,5-Dihydro-1H-imidazol-2-yl)-2-(3,5-dimethyl-isoxazol-4-yl)-indol-1-yl]-phenol;
1-(4-Hydroxy-phenyl)-2-(4-methyl-imidazol-1-yl)-1H-indole-3-carbonitrile;
1-(4-Hydroxy-phenyl)-2-(1H-pyrazol-3-yl)-1H-indole-3-carbonitrile;
1-(3-Chloro-4-hydroxy-phenyl)-2-(1-methyl-1H-pyrazol-4-yl)-1H-indole-3-carbonitrile;
1-(4-Hydroxy-phenyl)-2-prop-1-ynyl-1H-indole-3-carboxylic acid amide; or
1-(4-Hydroxy-phenyl)-2-thiazol-2-yl-1H-indole-3-carboxylic acid.

4. A kit as claimed in claim 1, wherein the platinum-containing anti-cancer drug is cisplatin or carboplatin.

5. A method for the treatment of mesothelioma in a patient, comprising
a) administering an ERβ agonist to the patient, and then after a time, t, of up to 24 hours,
b) administering a platinum-containing anti-cancer drug to the patient.

6. The method as claimed in claim 5, wherein the platinum-containing anti-cancer drug is cisplatin.

7. The method as claimed in claim 5, wherein the ERβ agonist is a compound of formula (III) or a salt or an ester thereof,

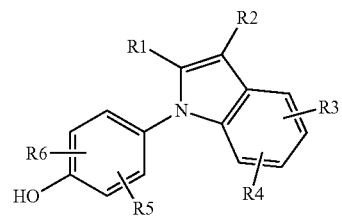

(III)

wherein $R^1$ is selected from the group consisting of halogen, cyano, nitro, $OR^A$, $N(R^B)_2$, —C(O)$C_{1-4}$alkyl, —SO$_2$$C_{1-4}$alkyl, $C_{1-6}$alkyl, $C_{2-6}$alkenyl, $C_{2-6}$alkynyl, halo$C_{1-6}$alkyl, dihalo$C_{1-6}$alkyl, trihalo$C_{1-6}$alkyl, halo$C_{2-6}$alkenyl, dihalo$C_{2-6}$alkenyl, trihalo$C_{2-6}$alkenyl, cyano$C_{1-6}$alkyl, $C_{1-4}$alkoxy$C_{1-6}$ alkyl, $C_{3-8}$cycloalkyl, $C_{3-8}$cycloalkyl$C_{1-6}$ alkyl, phenyl, benzyl, and 5-10 membered heterocyclyl, wherein said phenyl, benzyl or heterocyclyl group can be either unsubstituted or substituted with from 1 to 3 substituents, each substituent being selected from the group consisting of $OR^A$, halogen, cyano, nitro, —C(O)$C_{1-4}$alkyl, $C_{1-6}$alkyl, $C_{2-6}$alkenyl, $C_{2-6}$alkynyl, halo$C_{1-6}$ alkyl, dihalo$C_{1-6}$ alkyl and trihalo$C_{1-6}$alkyl;

$R^2$ is selected from the group consisting of halogen, cyano, nitro, $OR^A$, $N(R^B)_2$, N(OH)$_2$, —C(O)$C_{1-4}$alkyl optionally substituted with from 1 to 3 halogens, —SO$_2$$C_{1-4}$alkyl, —C(O)NH—OH, —C(NH$_2$)=N—OH, —C(CO$_2$H)=N—OH, —C(NH$_2$)=NH, —C(NH $C_{1-4}$alkyl)=NH, —C(O—$C_{1-4}$alkyl)=NH, —C(NH$_2$)=N—NH$_2$, —NH—C(NH$_2$)=NH, —NH—C(O)NH$_2$, —N=C(—NH—CH$_2$CH$_2$—NH—), —S—CN, —S—C(NH$_2$)=NH, —S—C(NH$_2$)=N—OH, —CO$_2$H, —CH$_2$—CO$_2$H, —CH(OH)CO$_2$H, —C(O)CO$_2$H, SO$_3$H, CH$_2$SO$_3$H, $C_{1-6}$alkyl, halo$C_{1-6}$alkyl, dihalo$C_{1-6}$alkyl, trihalo$C_{1-6}$alkyl, cyano$C_{1-6}$alkyl, $C_{1-4}$alkoxy$C_{1-6}$ alkyl, $C_{2-6}$alkenyl, $C_{2-6}$alkynyl, $C_{3-8}$cycloalkyl, $C_{3-8}$cycloalkyl$C_{1-6}$alkyl, phenyl, benzyl and 5-10 membered heterocyclyl wherein said phenyl, benzyl or heterocyclyl group can be either unsubstituted or substituted with from 1 to 3 substituents each substituent being selected from the group consisting of $OR^A$, halogen, cyano, nitro, $C_{1-6}$alkyl, $C_{2-6}$alkenyl, $C_{2-6}$alkynyl, halo$C_{1-6}$alkyl, dihalo$C_{1-6}$alkyl and trihalo$C_{1-6}$alkyl; provided that if one of $R^1$ and $R^2$ represents halogen, the other must represent a group other than halogen;

each of $R^3$, $R^4$, $R^5$ and $R^6$ is independently selected from the group consisting of hydrogen, $OR^A$, halogen, cyano, nitro, $C_{1-6}$alkyl, $C_{2-6}$alkenyl, $C_{2-6}$alkynyl, halo$C_{1-6}$alkyl, dihalo$C_{1-6}$alkyl and trihalo$C_{1-6}$alkyl;

each $R^A$ is independently selected from the group consisting of hydrogen, $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, $C_{6-10}$aryl and $C_{6-10}$aryl$C_{1-6}$alkyl, each optionally substituted by from 1 to 3 halogen atoms; and each $R^B$ is independently selected from the group consisting of hydrogen, $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, $C_{6-10}$aryl and $C_{6-10}$aryl$C_{1-6}$alkyl, each optionally substituted by from 1 to 3 halogen atoms;

with the proviso that the compound of formula (III) is not

4-[3-(4,5-Dihydro-1H-imidazol-2-yl)-2-(3,5-dimethyl-isoxazol-4-yl)-indol-1-yl]-phenol;

1-(4-Hydroxy-phenyl)-2-(4-methyl-imidazol-1-yl)-1H-indole-3-carbonitrile;

1-(4-Hydroxy-phenyl)-2-(1H-pyrazol-3-yl)-1H-indole-3-carbonitrile;

1-(3-Chloro-4-hydroxy-phenyl)-2-(1-methyl-1H-pyrazol-4-yl)-1H-indole-3-carbonitrile;

1-(4-Hydroxy-phenyl)-2-prop-1-ynyl-1H-indole-3-carboxylic acid amide; or 1-(4-Hydroxy-phenyl)-2-thiazol-2-yl-1H-indole-3-carboxylic acid.

8. The method as claimed in claim 7, wherein the ERβ agonist is a compound having the formula:

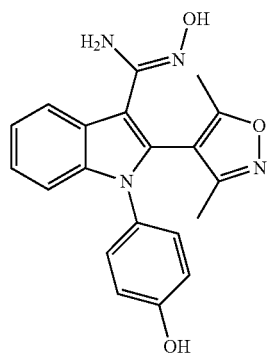

(I)

or a salt or an ester thereof.

9. The method as claimed in claim 5, wherein the mesothelioma is malignant pleural mesothelioma.

10. The method as claimed in claim 5, further comprising administering a further chemotherapeutic drug.

11. The method as claimed in claim 10, wherein the further chemotherapeutic drug is pemetrexed.

12. The method as claimed in claim 11, wherein the pemetrexed is administered after administration of the ERβ agonist.

13. The method as claimed in claim 5, wherein t is up to about 8 hours.

14. The method as claimed in claim 13, wherein the ERβ agonist is greater than 200 times selective for the estrogen receptor β-subtype over the estrogen receptor α-subtype.

15. A method as claimed in claim 7, wherein the platinum-containing anti-cancer drug is cisplatin.

16. A method as claimed in claim 8, wherein the platinum-containing anti-cancer drug is cisplatin.

17. A method as claimed in claim 11, wherein the pemetrexed is administered after administration of the ERβ agonist and before administration of the platinum-containing anti-cancer drug.

18. A method as claimed in claim 5, wherein t is up to 4 hours.

* * * * *

UNITED STATES PATENT AND TRADEMARK OFFICE
CERTIFICATE OF CORRECTION

PATENT NO. : 9,974,776 B2
APPLICATION NO. : 15/101132
DATED : May 22, 2018
INVENTOR(S) : Stefan Nilsson et al.

Page 1 of 1

It is certified that error appears in the above-identified patent and that said Letters Patent is hereby corrected as shown below:

On the Title Page

At Item (71) please replace the Applicant:
"Karo Pharma AB, Stockholm (SE)"
With:
--Oasmia Pharmaceutical AB, Uppsala (SE)--

Below the listing of inventors, please add Assignee Item (73):
--(73) Assignee: Oasmia Pharmaceutical AB, Uppsala (SE)--

Signed and Sealed this
Twenty-fifth Day of September, 2018

Andrei Iancu
*Director of the United States Patent and Trademark Office*